United States Patent [19]

Carson

[11] Patent Number: 5,425,390
[45] Date of Patent: Jun. 20, 1995

[54] PURGING METHOD

[75] Inventor: Douglas T. Carson, Lincoln, Nebr.

[73] Assignee: Isco, Inc., Lincoln, Nebr.

[21] Appl. No.: 132,562

[22] Filed: Oct. 6, 1993

Related U.S. Application Data

[60] Division of Ser. No. 937,493, Aug. 28, 1992, Pat. No. 5,280,721, which is a continuation-in-part of Ser. No. 592,960, Oct. 4, 1990, Pat. No. 5,275,042.

[51] Int. Cl.⁶ ............................................. G05D 16/04
[52] U.S. Cl. ...................................... 137/14; 137/469; 137/624.14
[58] Field of Search ...................... 137/469, 624.14, 14

[56] References Cited

U.S. PATENT DOCUMENTS

| | | |
|---|---|---|
| 3,087,335 | 4/1963 | Cavenah . |
| 3,301,050 | 1/1967 | McNulty . |
| 3,633,417 | 1/1972 | Montague . |
| 3,638,490 | 2/1972 | Buettner . |
| 3,727,459 | 4/1973 | Buettner . |
| 4,034,607 | 7/1977 | Martig, Jr. . |
| 4,127,032 | 11/1978 | Martig, Jr. . |
| 4,186,876 | 2/1980 | Clark et al. . |
| 4,200,120 | 4/1980 | Kimata et al. . |
| 4,367,652 | 1/1983 | Venuso . |
| 4,534,914 | 8/1985 | Takahashi et al. ......... 137/624.14 X |
| 4,571,997 | 2/1986 | Kepple et al. . |
| 4,694,692 | 9/1987 | Brown et al. . |
| 4,708,018 | 11/1987 | Brown . |
| 5,049,008 | 9/1991 | Baillie ............................ 137/469 X |

FOREIGN PATENT DOCUMENTS

2424454B4 11/1979 Germany .

Primary Examiner—Gerald A. Michalsky
Attorney, Agent, or Firm—Vincent L. Carney

[57] ABSTRACT

To measure flow rates, the cross-sectional shape of the flow path is changed by inserting a multiple position gate into the flow path and altering the position of the gate to maintain the head of liquid constant with a reduced flow cross section. The position of the multiple position gate is correlated with the depth as measured with a bubbler to provide an indication of flow rate. To purge the bubbler line, a purge tank is located near the bubbler line. At timed periods or as manually initiated the controller causes an increase in pressure in accumulator portion of the purge tank. When a predetermined pressure is reached, a purge valve in the purge tank opens, rapidly allowing a burst of air at a substantial pressure and velocity to flow through the bubbler line to remove any material adhering to the bubbler outlet port. For this purpose, the purge tank acts as an accumulator until the pressure in the tank against the effective area of the inner portion of a purge valve element overcomes the resisting force of a spring, at which time the valve element moves slightly, permitting air to flow over a larger area of the valve element. This increases the area receiving the accumulator air pressure to include an outer portion of the valve element and this increased effective pressure area of the valve increases the force rapidly to cause the valve to snap open.

6 Claims, 11 Drawing Sheets

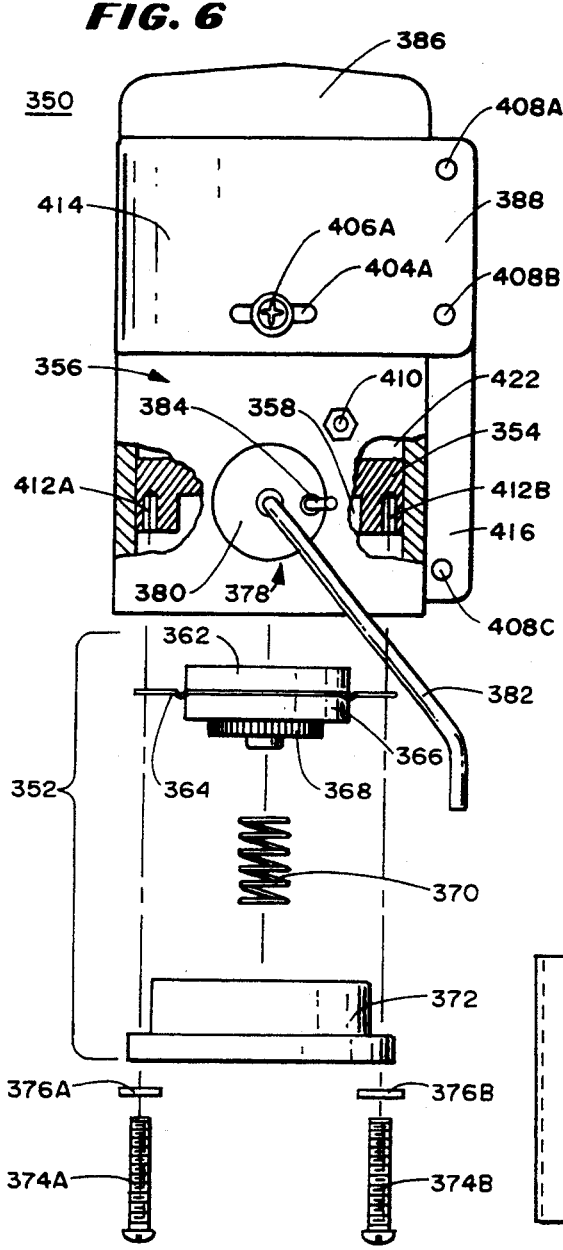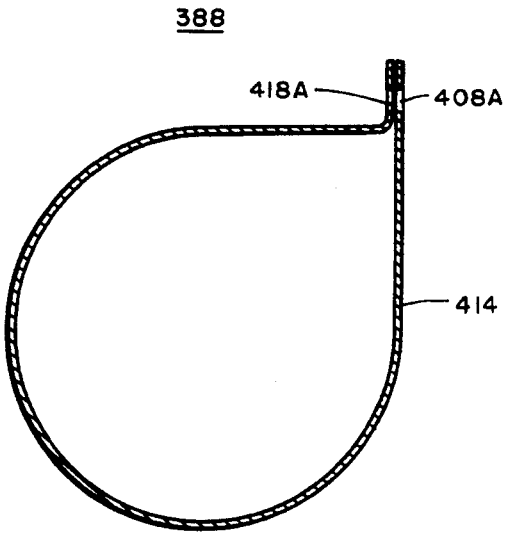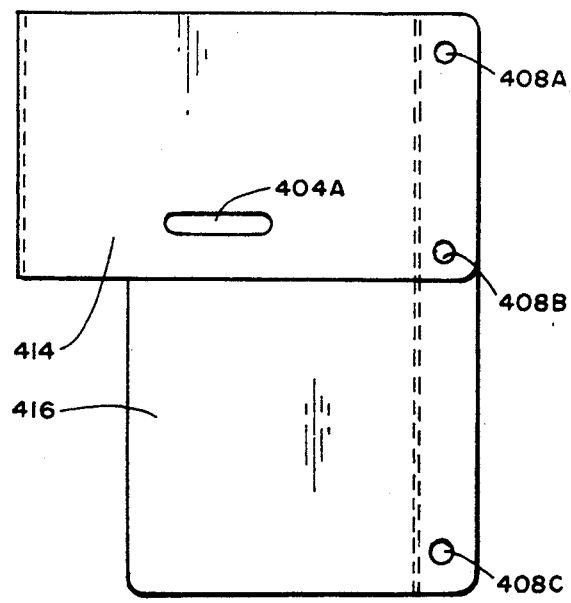

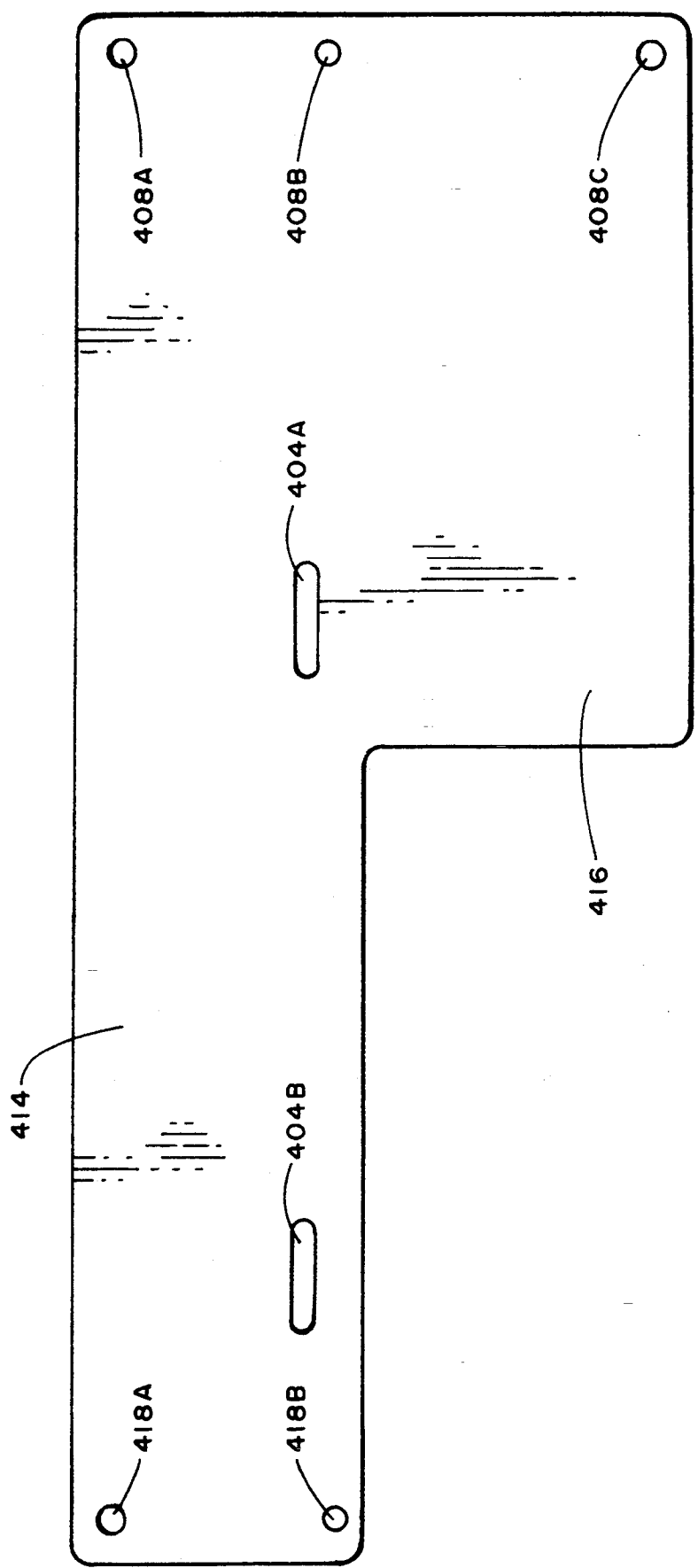

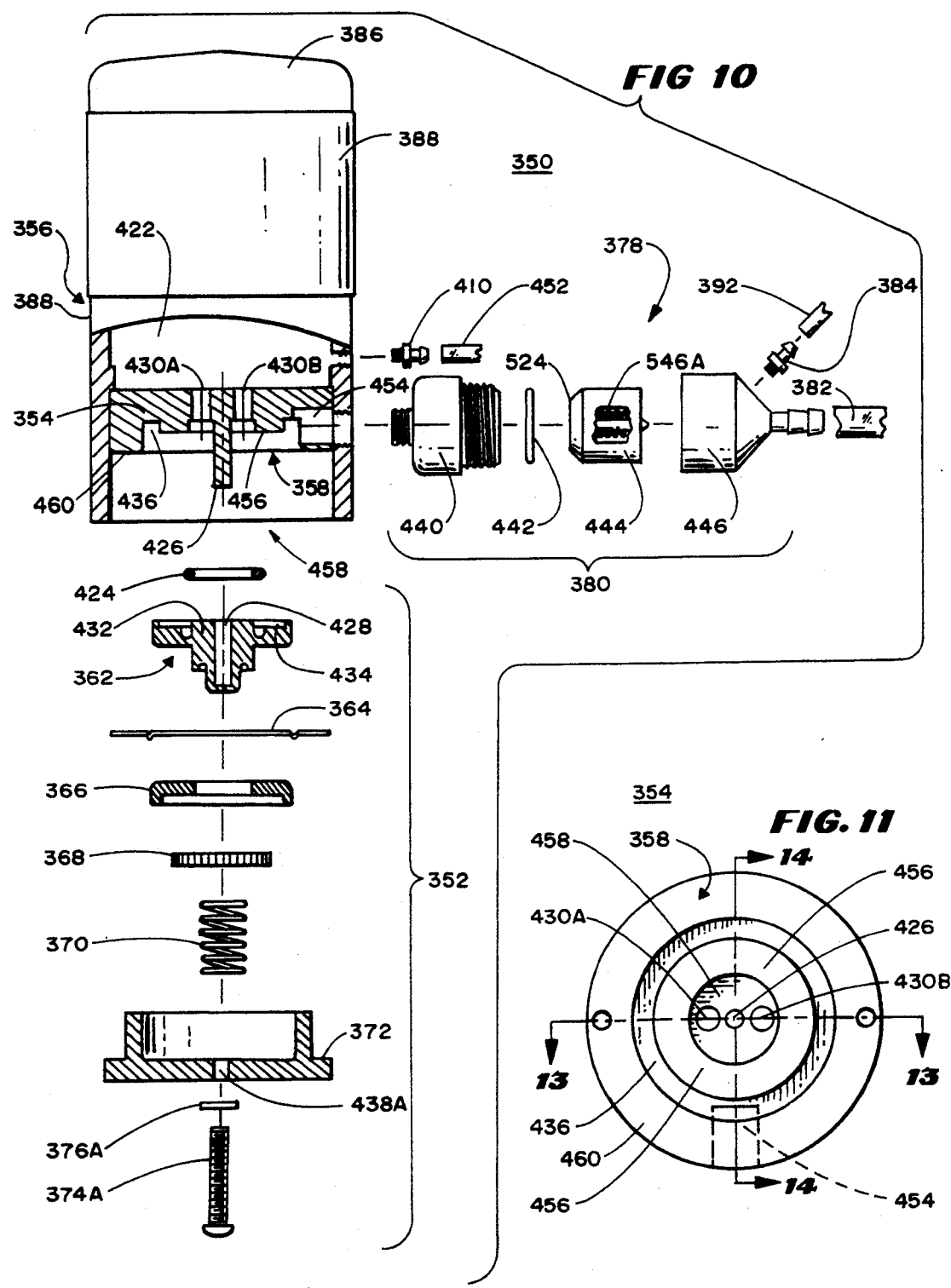

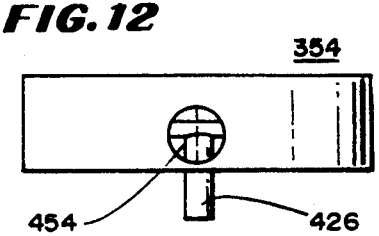
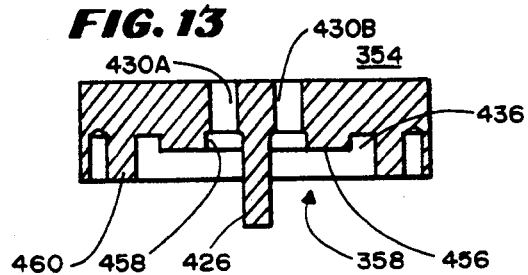
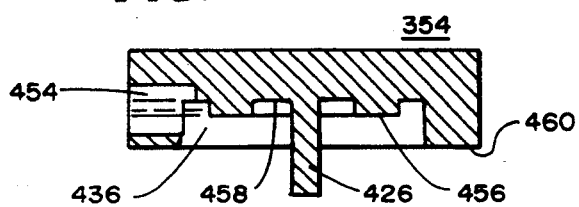
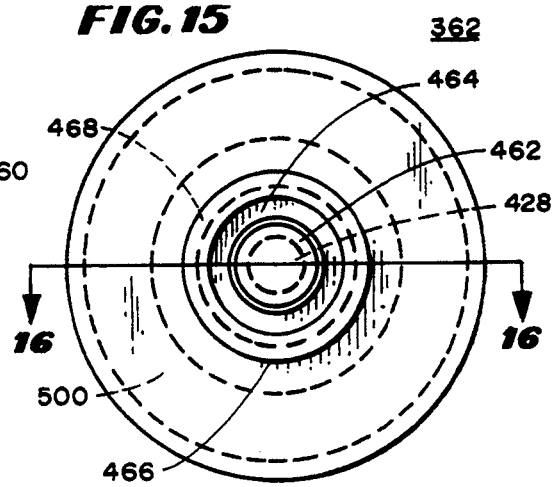
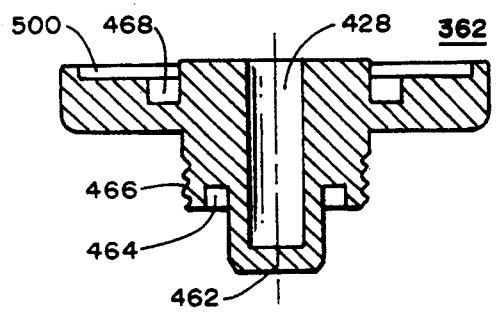
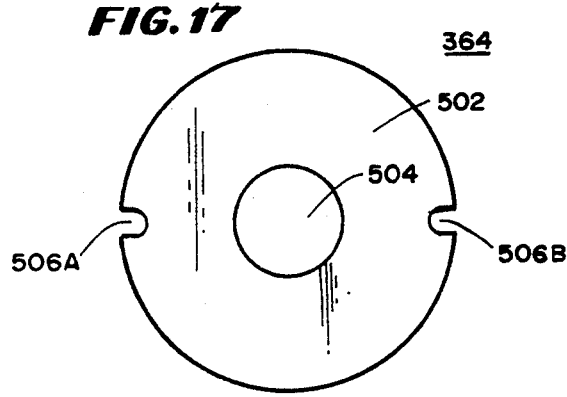
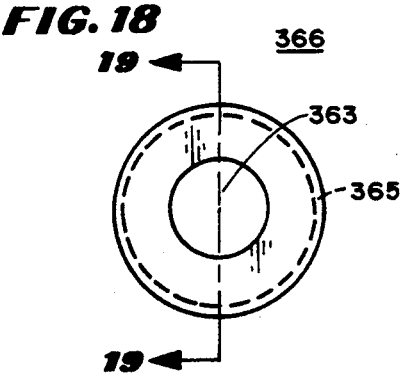
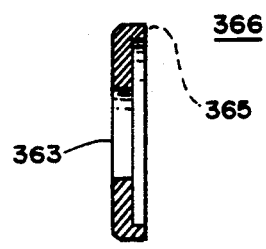

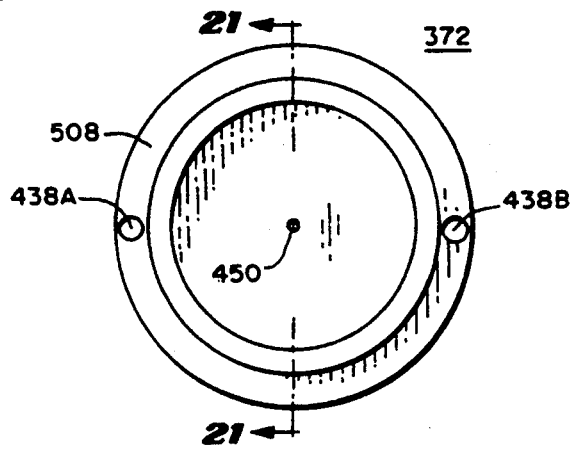
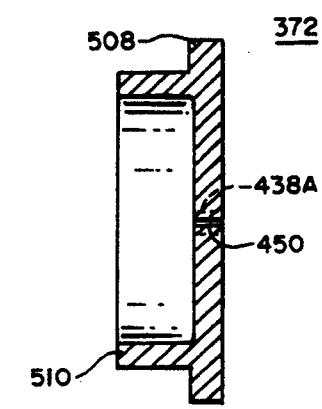
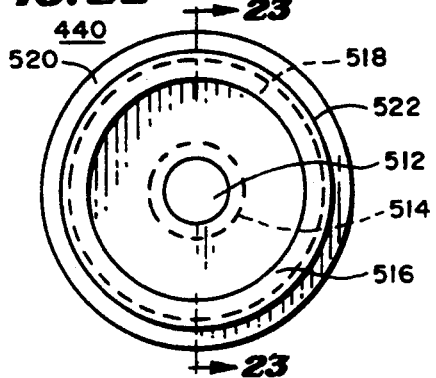
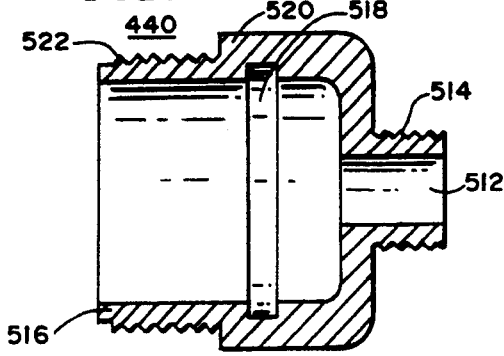
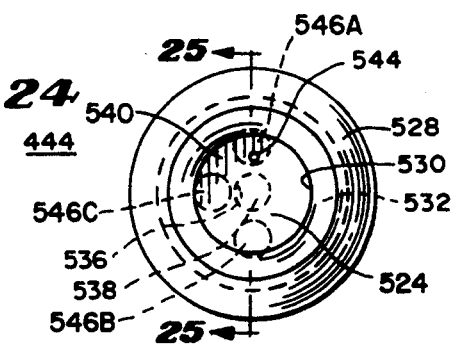
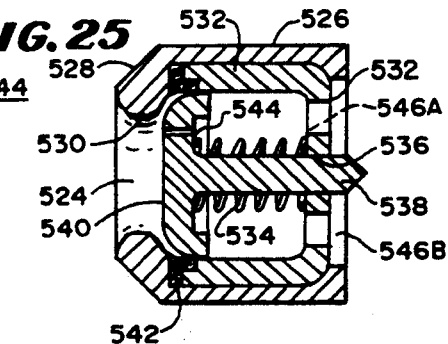
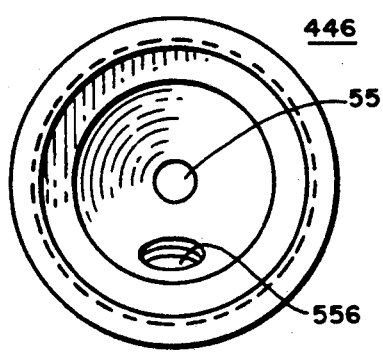
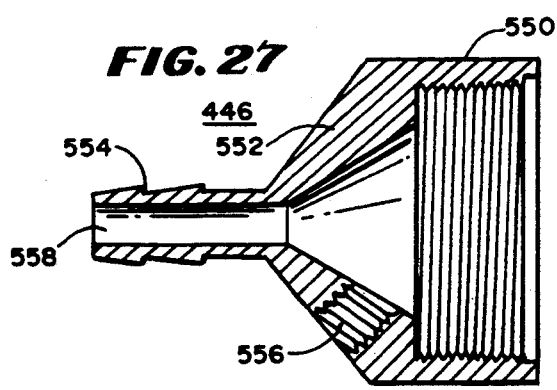

PURGING METHOD

RELATED CASES

This application is a division of U.S. patent application Ser. No. 07/937,493, filed Aug. 28, 1992, by Carson et al. now U.S. Pat. No. 5,280,721, for PURGE SYSTEM, which is a continuation-in-part of U.S. application Ser. No. 07/592960 filed by Carson, et al. on Oct. 4, 1990, now U.S. Pat. No. 5,275,042 for VARIABLE DATA FLOW ANALYZING METHOD AND APPARATUS.

BACKGROUND OF THE INVENTION

This invention relates to liquid depth measuring apparatus and methods, such as for example, are used in flow-rate measurements and in liquid sampling.

One class of flow meter performs depth measurements in a known flow path. For such a measurement, a depth measuring instrument such as a bubbler is used. The known flow paths may be controlled by a movable gate or obstruction in a flow stream that alters the flow to enable easier measurement of flow rate.

In one type of prior art bubbler, clogging is reduced by purging the outlet orifice of the bubbler from time to time with a faster flowing stream of air to clear the orifice. One such bubbler includes a purge system that accumulates air under pressure in a tank and opens the tank periodically to cause a high pressure surge of air to clear the bubbler.

In a prior art purge system of this type, the purge system includes a solenoid operated valve to open the tank to the bubbler line. The tanks have been generally located near a controller and remote from the bubbler outlet port. It has from time to time been proposed to locate the tank closer to the outlet port of the bubbler but this it not known to have been implemented. The prior art arrangement in which a solenoid operated valve opens an air tank near the controller has the disadvantage of requiring a long air line between the solenoid operated valve and the bubbler outlet and the proposed system with a tank close to the bubbler outlet would have had the disadvantage of requiring an electric line to a location in or near the water. Long electric lines increase the possibility of explosions from methane gas.

SUMMARY OF THE INVENTION

Accordingly, it is an object of the invention to provide a novel depth measuring instrument.

It is a further object of the invention to provide a novel bubbler.

It is a still further object of the invention to provide a novel technique for purging an underwater measuring instrument.

It is a still further object of the invention to provide a novel method for measuring flow rates of flowing fluids.

It is a still further object of the invention to provide a novel method for drawing samples from liquids to be analyzed.

It is a still further object of the invention to provide a novel method for altering the flow path of flowing liquids.

It is a still further object of the invention to provide a novel method for calibrating flow meters and depth measuring devices for liquids.

It is a still further object of the invention to provide a novel method for increasing the depth of moving liquids to permit easier measurement of the liquids.

It is a still further object of the invention to provide a novel method for measuring characteristics of streams which method is sufficiently versatile to make such measurements at either low flow rates or high flow rates.

In accordance with the above and further objects of the invention, flow rates in a flow path are measured by changing the shape of the flow path with a barrier, determining the position of the barrier, determining a characteristic of the flow path, and determining the flow rate. In this technique, the head of liquid pressure is measured with a bubbler and used with other measurements to determine the flow rate.

In one mode of operation, the barrier is maintained in a position such that the height of the fluid on the upstream side of the barrier remains constant at a height higher than in the unobstructed flow path, wherein the measurement is made at a higher head of pressure and variations in barrier position relate to flow rate. In another mode of operation, the barrier is substantially removed from the flow path when the height of the fluid on the upstream side of the barrier reaches a predetermined height. Advantageously, liquid is sampled upstream from the barrier, whereby samples may be taken from fluid having a substantial depth.

For calibration of a bubbler used to measure upstream depth, a zero measurement is periodically obtained by opening a conduit to the atmosphere connected to the housing of the bubbler wherein the sensor is exposed to atmospheric pressure. The flow path for the bubbler is protected by a shield and is kept clean by opening the gate to flush accumulated solids downstream. The flushing may also be done automatically upon sensing excessive solids near the barrier such as by the reflection of ultrasonic waves from the solids.

In the preferred embodiment, the bubbler may be purged by a separate purge tank which builds up pressure and releases it at high pressure into the bubbler outlet port to force the outlet port open by removing debris. Periodically, in addition to the purging device, a larger bubble is caused to be emitted to further maintain the port clear of debris. Calibration cycles are normally activated under control of a central programmer.

The water flow-rate measuring and liquid sampling apparatus is more fully described in U.S. patent application Ser. No. 07/592960, filed Oct. 4, 1990 in the name of Carson et al., now U.S. Pat. No. 5,275,042. This invention however differs from the apparatus in that disclosure in that the depth measuring bubbler therein has been improved by the addition of a purge apparatus designed to improve the reliability of measurements and their precision in streams carrying potential bubbler-outlet-port clogging materials. The disclosure of the aforesaid patent application is incorporated herein by reference.

To purge the bubbler line, a purge tank is located in the near vicinity of the bubbler line and connected to a controller with electronics, a valve and a pump or reservoir that are located much further away. At timed periods or as manually initiated, the controller starts the pump or connects the pump to the tank and increases the pressure in the line to the pressure of an accumulator portion of the purge tank. When a predetermined pressure is reached, a purge valve in the purge tank opens rapidly allowing a burst of air at a substantial pressure and velocity to flow through the bubbler line to remove any material adhering to the bubbler outlet port. The predetermined pressure is set by a biasing member related to the head of pressure against which the air is to be released.

For this purpose, the purge tank acts as an accumulator until the pressure in the tank against the effective area of an inner portion of a purge valve element overcomes the resisting force of a spring, at which time the valve element moves slightly, permitting air to flow over a larger area of the valve element. This increases the area receiving the accumulator air pressure to include an outer portion of the valve element and this increased effective pressure area of the valve increases the force rapidly to cause the valve to snap open.

Because the valve is able to automatically release fluid and accumulate fluid at periods of time related to the pressure setting of the biasing member and the pumping rate of fluid into the accumulator, it has been proposed that the valve may be used for other purposes such as to control the cycling of a bladder pump of the type that repetitively inflates and deflates a bladder to change the volume of a pumping chamber and thus pump fluid.

In making flow rate measurements using the bubbler, a flow housing having a tube with a flow path therethrough, an inlet and an exit is mounted to the flow path with a barrier for changing the depth of the flow path incorporated therein. Depth is measured with the bubbler mounted in the housing upstream of the barrier. The barrier comprises a gate mounted in said flow path, means for moving said gate such that said gate can be positioned in any of open, closed and a plurality of positions between the open and closed position relative to said flow path. By measuring the depth at different positions of the barrier and correlating this depth with the barrier position, the flow rate is measured.

From the above summary, it can be understood that the novel method and apparatus of this invention has several advantages, such as for example: (1) it is relatively simple, inexpensive and easy to use; (2) it permits relatively precise depth measurements, even in flow streams carrying material Capable of blocking a bubbler outlet port; (3) it is capable of cooperating with a versatile apparatus that can be used both to measure flow rates and take samples in a wide variety of streams and at a wide variety of different depths of flow and flow rates; (4) it is capable of great precision under difficult measuring conditions; (5) the apparatus can be used to perform a number of different measuring methods; (6) the valve can be used without electrical connection at the valve itself; and (7) it permits high-volumetric-rate air purging operations using a source near the bubbler outlet port without electrical connection.

SUMMARY OF THE DRAWINGS

The above-noted and other features of the invention will be better understood from the following detailed description when considered in connection with the accompanying drawings in which:

FIG. 6 is a front elevational view, partly exploded and partly broken away of a purge tank used in the embodiments of FIGS. 1–5;

FIG. 7 is an elevational view of a portion of a bracket for the tank of FIG. 7;

FIG. 8 shows a side developed view of the bracket of FIG. 6;

FIG. 9 shows the bracket of FIGS. 7 and 8 as an outwardly unfolded metal blank adapted to be bent into the bracket of FIGS. 7 and 8;

FIG. 10 is a side elevational view, partly exploded and partly broken away of the embodiment of tank of FIG. 6;

FIGS. 11, 12, 13 and 14 are a bottom view, front elevational view, sectional view through lines 13—13 of FIG. 11 and sectional view through lines 14—14 of FIG. 11 respectively of a valve plate used in the embodiments of FIGS. 6 and 10;

FIGS. 15 and 16 are a bottom view and sectional view through lines 16—16 of FIG. 15 respectively of a valve element used in the embodiments of FIGS. 6 and 10;

FIG. 17 is a plan view of a diaphragm used in the embodiment of FIGS. 6 and 10;

FIGS. 18 and 19 are a bottom view and sectional view through lines 19—19 of FIG. 18, respectively, of a diaphragm retainer plate used in the embodiment of FIGS. 6 and 10;

FIGS. 20 and 21 are a bottom view and sectional view through lines 21—21 of FIG. 20, respectively, of an end plate used in the embodiment of FIGS. 6 and 10;

FIGS. 22 and 23 are an elevational view and sectional view through lines 23—23 of FIG. 22, respectively, of a check valve housing used in the embodiment of FIGS. 6 and 10;

FIGS. 24 and 25 are an elevational view and sectional view through lines 25—25 of FIG. 24, respectively, of a check valve used in the embodiments of FIGS. 6 and 10;

FIGS. 26 and 27 are an elevational view and a transverse sectional view respectively of the outlet assembly for the embodiment of purge tank of FIGS. 6 and 10.

DETAILED DESCRIPTION

Figure 1:
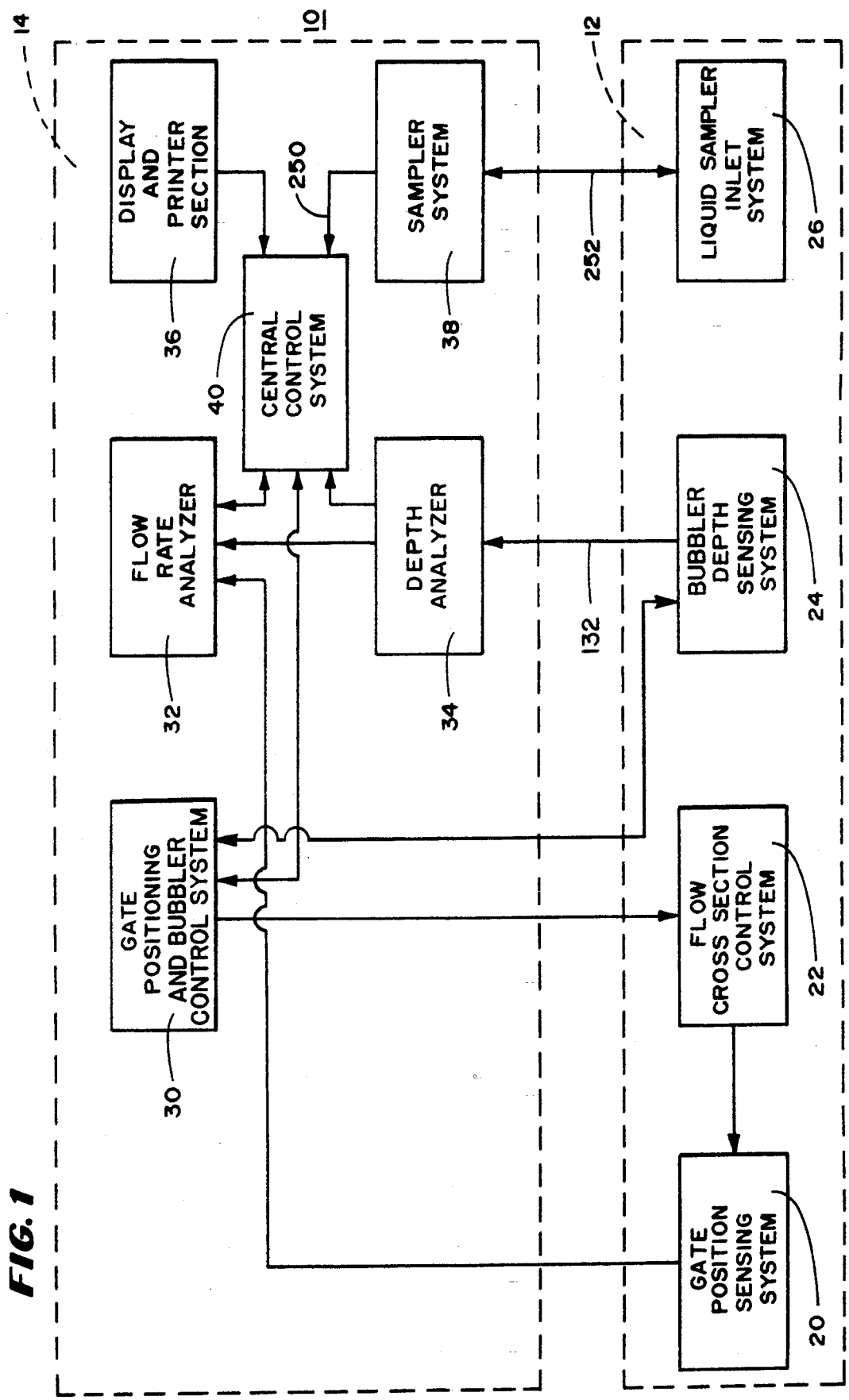
FIG. 1 is a block diagram of an embodiment of the invention.

In FIG. 1, there is shown one embodiment of a water flow rate measuring and liquid sampling apparatus 10 having a flow-stream local station 12, and a remote station 14 connected together with the flow-stream local station 12 being partly within the flow stream and generally connected together. It communicates with the remote station 14 through electrical conductors and pneumatic lines.

The flow-stream local station 12 and remote station 14 are arranged so as to alter the shape of a barrier to the flow stream and: (1) measure characteristics of the stream such as depth which permits a calculation of flow rate or other data; and (2) in some embodiments, draw samples of fluid for later analysis.

The flow-stream local station 12 includes a gate position sensing system 20, a flow cross section control system 22, a bubbler depth sensing system 24 and a liquid sampler inlet system 26. The flow cross section control system 22 and the gate position sensing system 20 are interconnected and communicate with the remote station 14 so that the gate position sensing system 20 indicates a gate position to the remote station 14 which in turn sends signals to control the flow cross section control system 22 and alters the barrier. In the preferred embodiment, the barrier is a gate-like structure that provides a greater or lower cross sectional area of flow projected into the direction of the flowing stream.

The bubbler depth sensing system 24 and the flow cross-section control system 22 also communicate with the remote station 14 to: (1) send back signals indicating depth, such as by indicating the head of pressure at a location in the bottom of the flow path; and (2) draw samples from an appropriate location for pumping to the remote station. The signals are interpreted in the light of the position of the barrier and the barrier can aid in creating a still location for appropriate samples to be drawn.

The remote station 14 includes a gate positioning and bubbler control system 30, a flow rate analyzer 32, a depth analyzer 34, a display and printer section 36, a sampler system 38 and a central control system 40. The depth analyzer 34 is electrically connected to the flow rate analyzer 32 and the gate positioning control system 30 to provide signals thereto indicating the depth of the flow stream.

The flow rate analyzer 32 receives signals from the gate position sensing system 20 and from the depth analyzer 34 and transmits signals to the central control system 40. The central control system 40, in response, transmits signals to the gate positioning control system 30 to control air and/or electrical signals controlling the gate and bubbler. The gate position sensing system 20 transmits information to the flow rate analyzer 32 and the flow rate analyzer 32 utilizes this information together with the information received from the depth anaylzer 34 to calculate flow rate. The sampler system 38 communicates with the liquid sampler inlet system 26 to periodically draw samples at times that are appropriate for later analysis.

The central control system 40 receives signals from the depth analyzer 34, the gate positioning control system 30, the flow rate analyzer 32, the display and printer section 36 and the sampler system 38. It utilizes those signals to control each of the above units and prepare data for display and printing by the display and printer section 36. Thus, the central control system 40 can make necessary calculations and store information such as look up tables related to coordination of depth and flow rate or can calculate values utilizing the Manning equations and display and print data as desired. It can also time and record the time of the drawing of samples by the sampler system 38.

Figure 2:
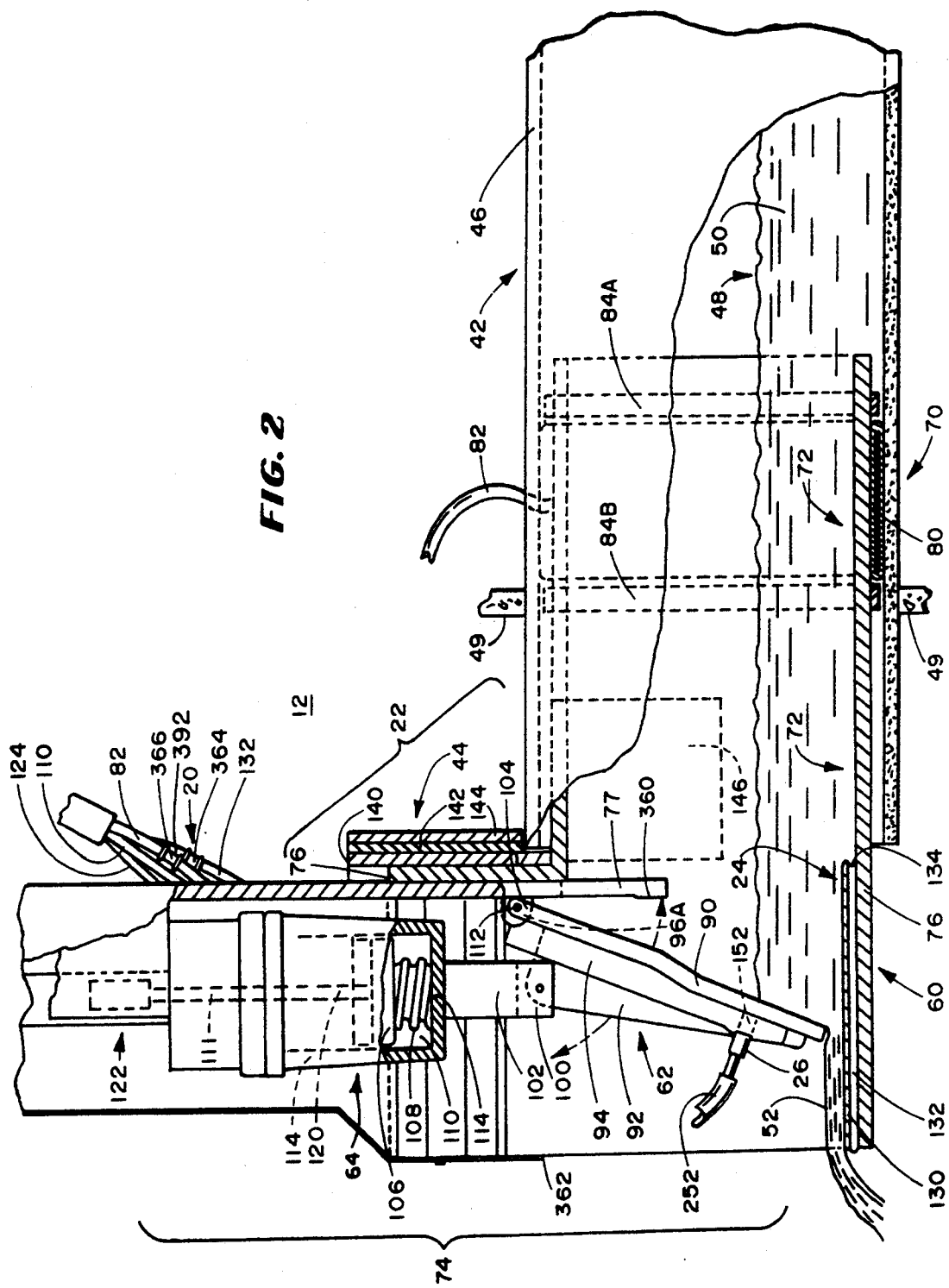
FIG. 2 is a simplified broken away partly schematic drawing of a portion of the embodiment of FIG. 1.

In FIG. 2, there is shown a broken away elevational view sectioned to show the flow-stream local station 12 mounted within a flow stream 42 and including the liquid sampler inlet system shown generally at 26, the depth sensing system shown generally at 24 within the flow stream 42. The flow cross section control system 22 is mounted in place in close cooperation with the gate position sensing system 20. A clamping unit 44 positions the flow path bed and the housing for level flow as explained hereinafter.

The flow stream 42 may be any flow bed for a liquid together with the liquid itself. In FIG. 2, there is shown as part of the flow stream 42, a pipe 46 with a bed of water 48 which may contain debris or sewage or the like such as would be carried by sewage lines in a city. In FIG. 2, the pipe 46 extends into a manhole indicated by the walls of 49 generally so that the flow cross section control system 22 extends partly into the pipe 46 and partly beyond it into the manhole.

The bed of water 48 for convenience is considered as having an upstream portion 50 which enters the flow cross section control system 22 and a downstream portion 52 which exits it beyond a barrier to be described hereinafter. The dividing line between the upstream portion 50 and downstream portion 52 of the flowbed is the barrier controlled by the flow cross section control system 22.

The flow cross section control system 22 includes a flow housing 60, a gate assembly 62 and a gate control assembly 64. The gate assembly 62 and gate control assembly 64 are mounted together so that the gate control assembly 64 controls the gate assembly 62 in forming a barrier to the upstream portion 50, which barrier changes its shape insofar as it projects a different profile upstream of the flow. The gate assembly 62 and gate control assembly 64 are mounted to the flow housing 60 by the clamping unit 44, which in turn, is mounted to the flow stream 42 to receive the flow of liquid 48.

To mount the flow housing 60 in position where it receives the flow of liquid 48 at the gate assembly 62 and gate control assembly 64 properly, the flow housing 60 includes a sealing section 70, a flowbed section 72, a gate housing section 74 and the clamping section 44. The gate control housing 74 includes within it the mechanism for positioning the gate assembly 64 and the gate position sensing system 20. The flowbed section 72 includes internal walls 76 which receive the water 48 or water combined with sewage or debris or the like from upstream and supports its flow downstream. It is sealed by the sealing section 70 to the flow bed or flow stream 42 so that all of the water or other liquid to be measured flows into the flowbed section 72. The gate housing section 74 is joined to the flowbed section 72 and clamping section 44 clamps the entire assembly in position to the flow stream 42.

In the preferred embodiment, the flow stream 42 is a cylindrical pipe and the internal walls 76 of the flowbed section 72 is a conformingly shaped cylinder slightly lower in outer diameter than the inner diameter of the walls of the pipe 46, forming a portion of the flow stream 42. However, the flow stream 42 may assume other shapes and the internal walls 76 will also take other shapes in such a case.

To mount the gate assembly 62, the gate control assembly 64 and gate position sensing system 20, the gate housing section 74 of the flow housing 60 includes internal walls which are rigidly mounted to or integrally formed with the internal walls 76 of the flowbed section 72 that extend upwardly so as to be usually, or in most installations above, the upstream portion 50. To this gate housing section 74 are mounted the gate position sensing system 20, the gate control assembly 64 and the gate assembly 62 which extends downwardly into the liquid 48 to divide the upstream portion 50 from the downstream portion 52. In FIG. 2, the gate housing section 74 is fragmentary and shown broken at its uppermost portion.

To seal the internal walls 76 against the walls of the pipe 46, the sealing section 70, in the preferred embodiment, includes a bladder 80, a pneumatic bladder tube 82 and retaining members 84A and 84B in one embodiment for sealing the bladder 80 to the internal walls 76. With this configuration, after the flow cross section control system 22 and gate position sensing system 20 are in place within the pipe 46, air may be applied to the bladder 80 through the pneumatic bladder tube 82 to inflate it and form a sealing connection between the internal walls 76 and the walls of the pipe 46.

To form a barrier to the flow of the liquid 48, the gate assembly 62 includes a plastic plate portion 90 and a plurality of integrally formed ridges extending from its surface, such as 92 and 94 in the preferred embodiment. One of those ridges centrally located cooperates with the gate control assembly 64 that pivots the gate upwardly away from the liquid stream 48 or downwardly into its surface and at greater depths to create a barrier in the liquid which will cause the upstream portion 50 to be higher than the downstream portion 52.

Figure 4:
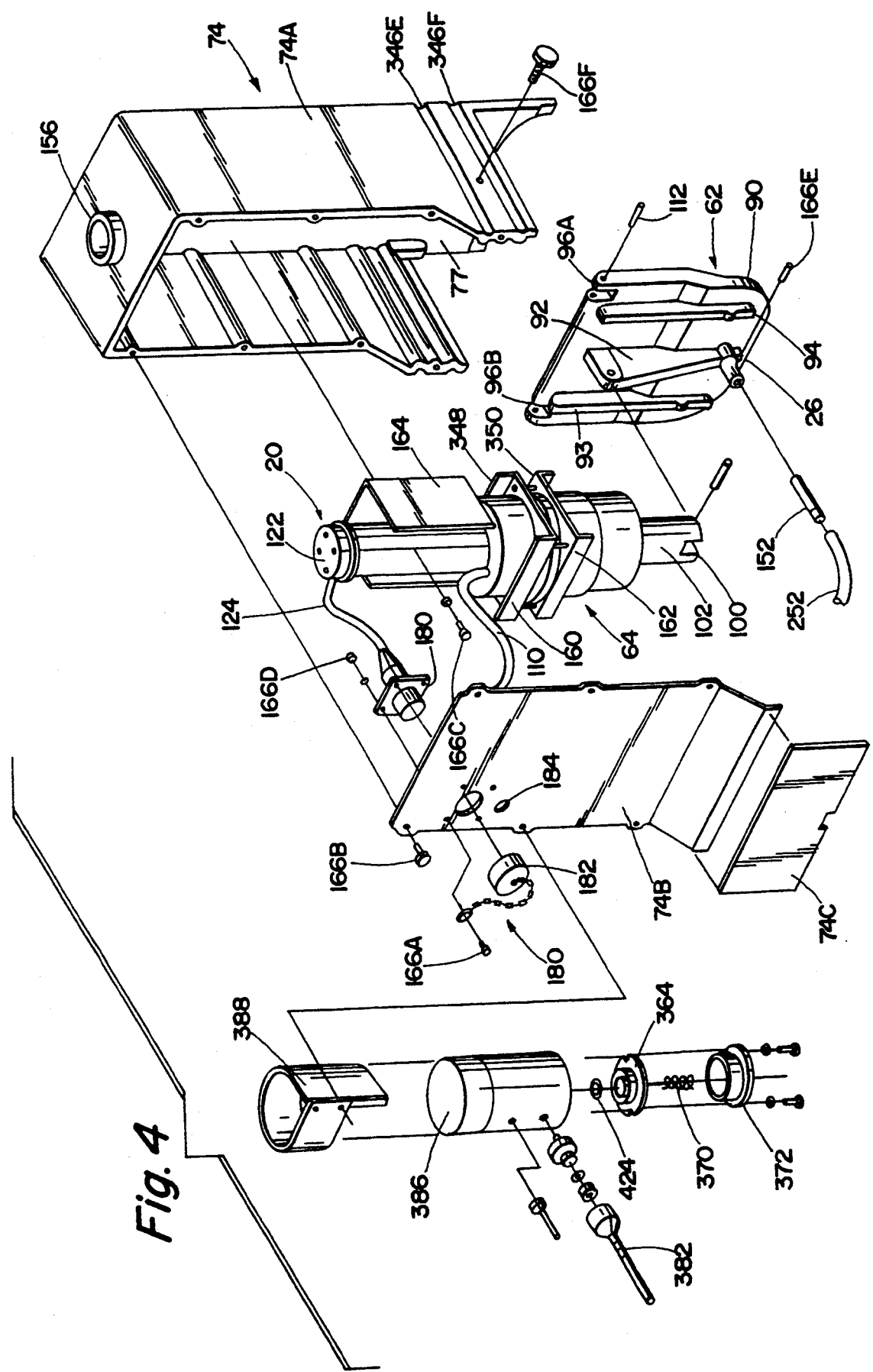
FIG. 4 is an exploded perspective view of a portion of the embodiment of FIGS. 1–3 from a viewpoint different from that of FIG. 3.

The plastic plate portion 90 includes two yokes, 96A unit and 96B, (96A only being shown in FIG. 2) cut into its end and pivotably mounted to one wall 77 of the gate control housing. The gate control assembly 64 includes a yoke 100, a piston shaft 102, an ear 104, a piston diaphragm 106, a helical compression spring 108, a pneumatic tube 110 and a piston 105 (not shown in FIG. 2). The piston shaft 102 is connected to the piston 105 under the diaphragm 106 at one end and at the other end has the yoke 100. The ear 104 is integrally formed with or fastened to the internal wall 77 of the gate housing 74 spaced from the movable piston shaft 102 and cooperates with a yoke 96A by receiving a pin 112. A similar ear cooperates with a yoke 76B (FIG. 4).

The yoke 100 similarly receives a pin and is pivotably mounted to the ridge 92 so that as it moves up and down, it causes movement of the plastic plate portion 90 with respect to the ear 104, which pivots about the pin 112 through the yoke 96. The helical compression spring 108 is mounted between the piston 106 and a wall 114 of a piston chamber within which the piston bladder 106 moves. Below the piston bladder 106, the helical compression spring 108 communicates with the cylinder so that air pressure applied by the tube 110 to the upper part of the piston chamber moves the piston and piston bladder 106 downwardly against the force of the compression spring 108. When the pressure is released, the spring 108 moves the piston 106 upwardly to move the shaft 102 upwardly, which in turn pivots the gate assembly 62 about the pin 112 upwardly and away from the bottom of the liquid 48. Similarly, pressure applied to the chamber wall 114 above the piston diaghram 106 through the tube 110 (see FIGS. 3 and 11 for location) moves the gate assembly 62 downwardly into increasing depths of the liquid 48, where it may be held by maintaining the gas pressure in the chamber.

The gate position sensing system 20 includes a shaft 120 and a position sensor 122. The shaft 120 is connected at one side to the piston 105 (under bladder 106) and at its other side to a core of the sensor 122 so that as the piston 105 moves upwardly and downwardly, the shaft 120 moves and causes the sensor 122 to generate a signal indicating the position of the piston 105 and therefore the gate assembly 62.

The position sensor 122, in the preferred embodiment, is a LVDT (linear variable-differential transformer) which generates a signal that varies linearly with shaft 120 movement. It is energized by two of the conductors 124 and applies a signal on two other conductors, all of which are in the cable 124.

The liquid sampler inlet system 26 includes a conduit which communicates in a typical manner through a fitting or the like, preferably in the gate assembly 62, for drawing under the control of a sampler system 38 (FIG. 1) periodic samples of fluid for analysis. It is generally located on the gate assembly 62 at a location which has sufficient depths, is sufficiently nonturbulent to draw representative samples and sufficiently turbulent to reduce clogging. Prior to drawing a sample, the gate assembly 62 may be opened so as to remove solids and then closed until the depth is sufficient for taking a sample.

To determine the depth of the fluid, a bubbler tube 132 is mounted adjacent to the bottom wall 76 of the flow path and under a protective cover and flat calibrating surface 130. The pressure measuring point or entrance to the housing of the bubble tube is at location 134 approximately 0 inches from the location of the gate to 2 feet when fully closed. It should be at a known elevation from the end of the gate assembly or the same elevation. The location is selected to be sufficiently far from the end of the wall 76 and of the gate so that neither the gate nor the flow of water from the end of the wall 76 into a manhole affect the measurement by velocity effects such as Venturi effects or by having an unusual rise or lowering of the liquid level at that point but sufficiently close to obtain scrubbing from the velocity of the liquid flowing over it.

To mount the flow cross section control system 22 to the flow stream 42 (pipe 46), an adjustable clamping unit 44 includes a bracket 140, a first adjustable clamp 142 and a second adjustable clamp 144. The first and second adjustable clamps 142-144 each include an adjustable plate with a curved clamp portion mounted thereto to grip the walls of the pipe 46, one curved clamp member being shown at 146 formed integrally with the outer plate of the second or outer adjustable clamp 144. The clamping plates 142 and 144 are pivotable about the bracket 140 and adjustable with respect to each other so that the flow cross section control system 22 may be positioned at different heights and angles with respect to the clamping means.

Figure 3:
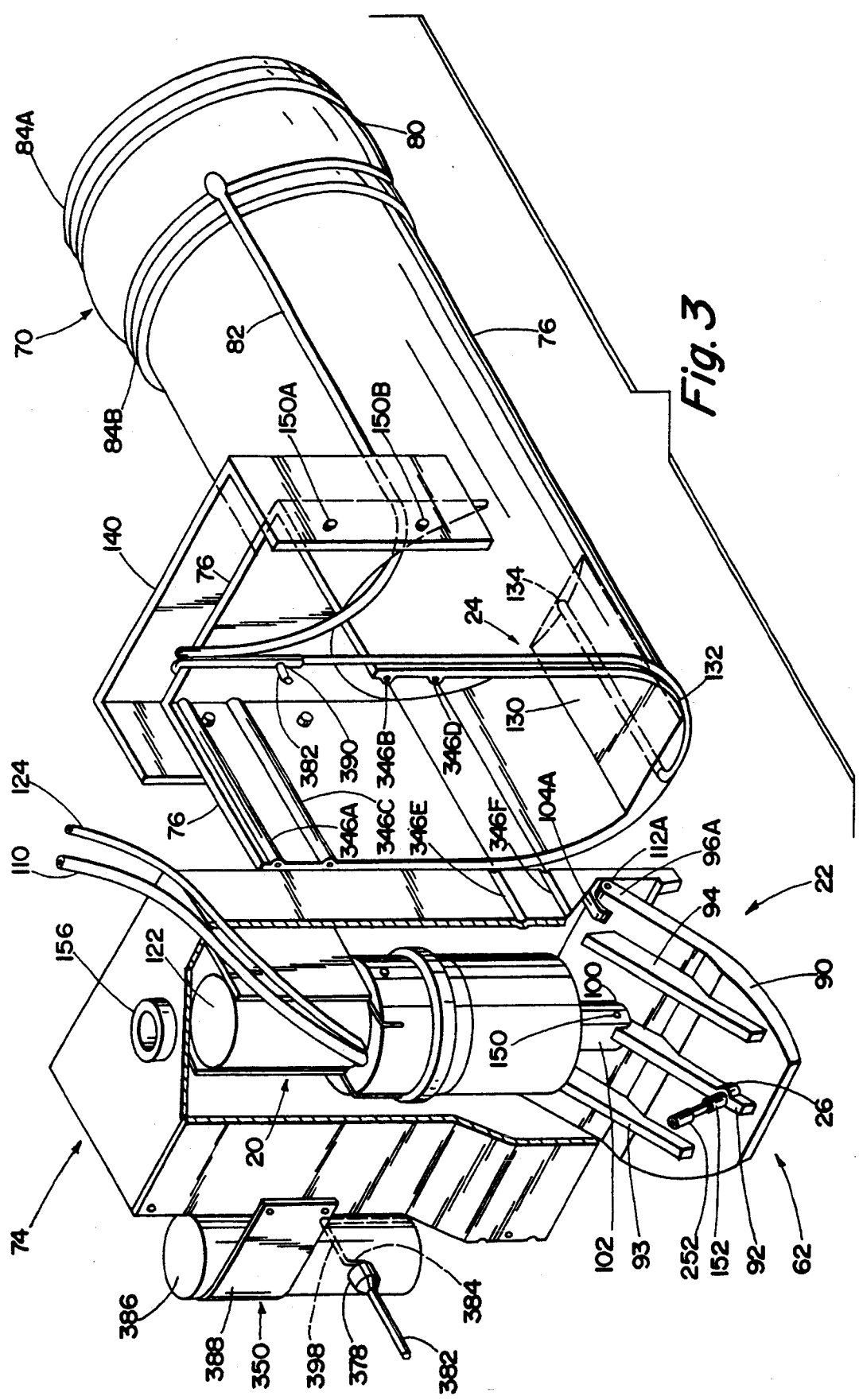
FIG. 3 is an exploded, fragmentary, broken away, perspective view of a flow path, variable position gate and measuring apparatus in accordance with the embodiment of FIG. 1.

In FIG. 3, there is shown an exploded perspective view partly broken away of the flow cross section control system 22, gate position sensing system 20 and depth sensing system 24 mounted together and showing only the bracket 140 of the clamping means.

As best shown in this view, the gate assembly 62 includes three reinforcing ribs 93, 92 and 94 with the rib 92 fitting within the yoke 100 of the shaft 102 and being pinned therein by a pin 150 for pivotable movement about the pins 112A and 112B (112B not shown in FIG. 3) through the ear 104A and 104B (ear 104B not shown in FIG. 3) and the yokes formed of the cutout portion 96A and 96B (96A only shown in FIG. 3) of the gate assembly 62 so that as the shaft 102 moves upwardly and downwardly, the gate is raised and lowered as the LVDT senses its position and transmits it through a cable 124 to the remote station 14 (FIG. 1).

A gate insert or opening 152 extends through the rib 92 and a plate 90 to face upstream, thus serving as a sample inlet 26. The samples are drawn to the surface through a tube 252. Sampling at this location provides representative samples. They are drawn within 15 minutes after closing the gate and as soon as the liquid is sufficiently high such as 3 or 4 minutes.

A bubble level 156 is mounted on top of the housing 74 and may be used in conjunction with the adjustable clamping unit 44 (FIG. 4) to cause the wall 76 to be horizontal for accurate measurement by an operator looking down so as to be free from the flow into the manhole.

The bracket 140 is generally shaped in cross section as a U facing on its side so as to provide a front surface and side wings which may be fastened by bolts to the wall 76, such as by the bolts 150A and 150B or by any other convenient fasteners and thus support a pivot point and locking screws (not shown in FIGS. 2 and 3) as well as the adjustable clamps 142 and 144 (FIG. 2).

As best shown in this view, a purge tank 350 is mounted to the walls of the gate housing section 74 and connected by a purge air line 382 to one leg of a tee connection 390. The other legs of the tee connection are connected in line with the bubbler tube 132 so that the line 382 communicates with the line 132 to provide an added flow of purge air therethrough during a purge cycle but is otherwise closed and out of the connection with the bubbler 132. With this arrangement, the purge assembly is connected near the bubbler outlet port and within three feet thereof, being connected on the port side of the restrictor 318 so as to be capable of providing an unrestricted high velocity flow of air to the bubbler outlet port for purging thereof.

It is also possible to connect the lines internally to the housing of the purge system instead of using a tee connection external. The external tee connection is used for clearity in FIG. 3.

In FIG. 4, there is shown another exploded perspective view of the gate position sensing system 20, the gate control assembly 64, and the gate assembly 62 as they are mounted together. As shown in this figure, the gate housing 74 includes a plurality of disassemblable sections 74A, 74B, and 74C to permit ready access to the gate assembly 62, gate position sensing system 20 and gate control assembly 64.

To support the gate assembly 62, the gate position sensing system 20, and the gate control assembly 64, the gate assembly 62 is mounted to the housing 74 by yokes 96A and 96B and the gate position sensing system 20 is mounted to the gate control assembly 64 by brackets 160 and 162 and to the housing 74 by bracket 164. The brackets and portions of the housing are held together by conventional screws, bolts, nuts and pins such as those shown at 166A-166F.

To seal a conductor 124 when not electrically connected and to provide a socket for connecting electrical wires, a connector 180 fits within the housing member 74B so that it may be sealed when not connected to a cable by cap 182. Similarly, the pneumatic conduit 110 for energizing the piston and thus the shaft 102 communicates with a connector 184 for connection to an external pneumatic tube. In the preferred embodiment, one connector is used for both pneumatic and electrical connectors.

As shown in this view, the purge tank 350 is mounted to the housing 74 by the bracket 388 to be readily attached to existing flow control systems and the bubblers used in them. It is connected to a portion of a measuring and sampling system near the port of a bubbler for easy connection on the port side of the restrictor. Of course, it could be used with other bubblers or other systems that need a burst of fluid such as to clear them.

Figure 5:
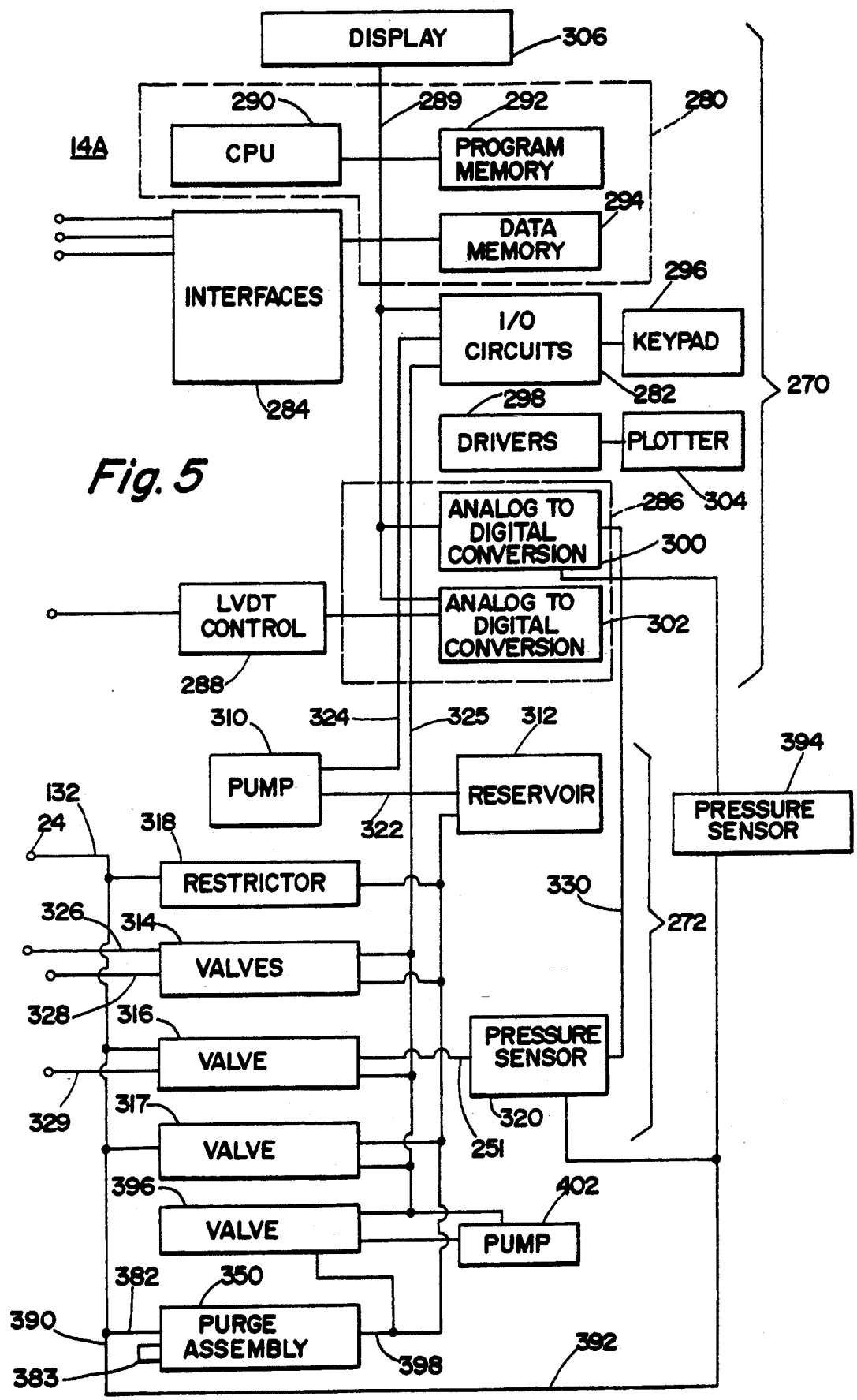
FIG. 5 is a block diagram of a portion of the embodiment of FIG. 1 for controlling the apparatus of FIGS. 2–4.
Figure 28:
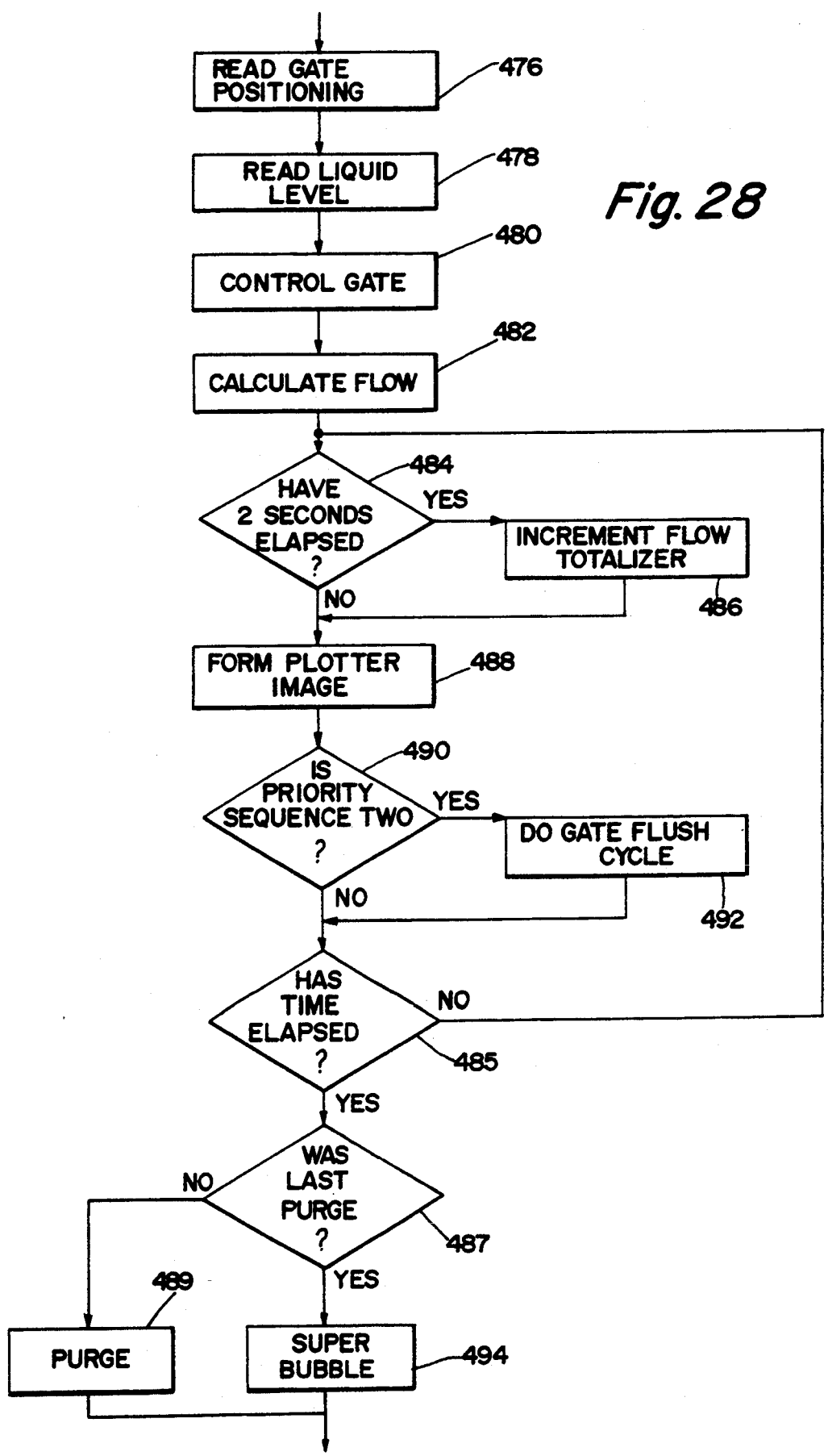
FIG. 28 is a flow diagram of a program used in the embodiment of the invention for purge operations.

In FIG. 5, there is shown a block diagram of another embodiment of remote station 14A similar to the embodiment 14 of FIG. 1 having an electronic portion 270 and an air portion 272. The embodiment 14A performs the same functions as the embodiment 14 of FIG. 1 but utilizes a standard microprocessor and a standard LVDT. The program used in the purge operation is attached hereto as Attachment A and a flow diagram in accordance therewith comprises FIGS. 28 to be described hereinafter.

The electronic portion 270 includes as its principal parts, a microprocessor 280, an input output section 282, certain interfaces 284, an analog to digital conversion section 286 and a LVDT control section 288. All of these sections communicate with the microprocessor 280 through a central bus 289 so that the microprocessor 280 can; (1) provide signals to the interface section 284; and (2) receive programming and data from and provide signals to the input-output circuits 282. Similarly, the analog to digital conversion section 286 serves as an interface for the microprocessor 280 and other units, being connected to the air portion 272 to receive analog pressure signals representing depth and to the LVDT control system 288 to receive buffered analog signals indicating gate position.

To provide as a centralized source of calculations and control operations, the microprocessor 280 includes a CPU (central processing unit) 290, a program memory 292 and a data memory 294. These units function together to make calculations and perform control operations. The program memory 292 includes inter alia a look-up table capable of providing flow rates in response to depth information and gate position information under the control of the central processing unit 290. The input-output circuits 282 receive information from a keypad 296, supply signals to certain drivers 298 for driving a plotter 304 in a manner known in the art, and receive and transmit signals from and to the microprocessor 280.

The interfaces 284 include buffering interfaces to provide signals received by it from the computer unit 280 to the sampler, the remote plotter and any other units with which it may be desirable to communicate but which require buffering different than that provided by the input-output circuits 282.

The analog to digital conversion section 286 includes two analog to digital converters 300 and 302, one of which is connected to receive analog signals from the LVDT control 288 which receives analog signals from the gate position sensing system 20 and buffers them for application to the analog to digital converter 302 and the other of which receives signals from the air portion 272 indicating pressure upon the depth sensing system 24 (FIG. 1). These units communicate with a display 306 to display data, with the computer system 280 for calculations and with the input-output circuits 282 for operating the driver 298 and plotter 304.

The central processing unit 290, in the preferred embodiment, is a Hitachi America, Ltd, Number HD64180RCP-6X available from the Hitachi America Ltd., Semi-Conductor and IC Division, 2210 O'Toole Avenue, San Jose, Calif. 95131. This is an 8-bit microprocessor referred to as a HD64180 8-bit Microprocessor.

The air portion 272 includes an air pump 310, an air reservoir 312, gate control valve 314, bubbler control valve 316, an air restrictor 318, a valve 317, a purge valve 396, a purge assembly 350, a pump 402 and a pressure sensor 320. The air pump 310 supplies air under pressure to reservoir 312 through a conduit 322 in response to signals received over an electrical conductor 324 from the input-output circuits 282. Pressure is supplied by the reservoir 312: (1) directly to the control valves 314 for the gate positioning control system 30 for positioning the gate assembly 62; and (2) through a restrictor 318 for operating a bubbler that includes a port 24 (FIGS. 1, 2 and 4). Valve 316 connects the pressure sensor 320 to atmosphere through conduit 329 for calibration or in another position to the bubbler port and restrictor to sense pressure.

To maintain the bubbler port clear, valve 317 when opened connects the reservoir to the bubbler port for a speed up super bubble. This valve may also be used for purging by holding it open for a longer time. The purge assembly 350 is connected by a purge air line 382 and a tee 390 to the bubbler tube 132. In the preferred embodiment, its air inlet is electrically connected to the reservoir 312 and a sensing outlet is electrically connected to the pressure sensor 320 or may be connected to a separate sensor 394. In either case, the electrical signal is converted to a digital signal and the program in the control section utilizes this signal to control the operation of the purge system. However, its air inlet may instead be connected through the solenoid control valve 396 which in turn communicates with the reservoir 312 or with a pump 402. If it communicates with the valve 396, the valve is electrically connected to the conductor 325 to receive a signal initiating a purge or in the alternative, the pump 402 is electrically connected to conductor 325 to be started and stopped.

To position the gate assembly 62, the gate assembly is moved and held: (1) down by applying pressurized air from the reservoir 312 to the compartment above piston 106 (FIG. 2) through a first conduit 326 by pulsing one of the valves 314 with a signal on conductor 324; and (2) upward by venting air to atmosphere through the other valve 314 to a conduit 328, in which case, the spring 108 (FIG. 2) moves the gate assembly 62 (FIG. 2) upwardly to the new position established by pressure in the reservoir above the piston 106. This motion causes the LVDT to provide a new signal to the control unit 288 as feedback for controlling the position of the gate assembly 62.

To calibrate the pressure sensor 320 and/or the pressure sensor 394, the valve 316 is mounted near the pressure sensor 320. To free the system from losses that vary with tube length, the restrictor is connected near the bubbler port 24 in the housing of the gate assembly. The valve 316: (1) is activated to vent the tube 252 to atmosphere through a conduit 329 in one position for calibration; and (2) to connect line 252 from the outlet of the restrictor 318 and outlet port 24 to conduit 251 to apply pressure representative to sensor 320 which in turn supplies an electrical signal on conductor 330 to the analog to digital converter 300.

The restrictor 318 in the preferred embodiment is mounted in the housing of the local station so that it is near the bubbler outlet port 24 and the pressure applied to the pressure sensor 320 is not affected by the length of bubbler tube extending to a location near or in the remote station. This bubbler tube may be long and may thus introduce pressure errors from resistance even if the bubbler tube is between the pressure controlling restrictor and the port 24 if it is long.

While in the preferred embodiment, the restrictor is mounted in the housing, it could be mounted at some other location, preferably near the port 24 if this is convenient. For example, it could be mounted within 10 or 15 feet of the port. By mounting this restrictor close to the port, a smaller diameter air tube can be used for the bubbler and this permits the air tube to fit within a small connector along with the air tube for controlling the gate control mechanism and the electrical conductors because the pressure drop in the tube can be compensated.

In FIG. 6, there is shown a partly-broken-away, partly-exploded elevational view of the bubbler purge system 350 having a bubbler purge system housing 386, a bracket 388, an accumulator assembly 356, a purge valve assembly 352 and an outlet assembly 378. Air from the reservoir 312 (FIG. 5) flows through line 398 (FIG. 5) and either directly into the accumulator assembly 356 or through the valve 396 (FIG. 5) into the accumulator assembly 356. This assembly is within the housing 386 and is cooperatively mounted to the purge valve assembly 352 and the outlet assembly 378 so that when the pressure in the accumulator assembly reaches a predetermined value, the valve assembly 352 opens a pathway into the outlet assembly 378 to purge the bubbler 132 (FIG. 5). Instead of receiving air from the reservoir 312, the accumulator assembly 356 may receive air directly from a pump 402 as described in connection with FIG. 5.

The bracket 388 is mounted to the bubbler gate housing 74 and for this purpose includes eyelets 408A and 408C to receive bolts or fasteners therefore. It surrounds and grips the purge assembly housing 386 and is further fastened by machine screws 406A and 406B (only 406A being shown in FIG. 6) which fit within the slots 404A and 404B respectively (only 404A being shown in FIG. 6).

To accumulate air under pressure, the accumulator assembly 356 includes an inlet port 410, a valve seat 358, a valve seat plate 354, and a compartment 422 occupying most of the interior of the housing 386. Tapped holes 412A and 412B in the valve seat plate 354 are used to fasten the valve assembly to the housing 386 in a manner to be described hereinafter. With this arrangement, the accumulator assembly 356 is mounted to the purge valve assembly 352 and the outlet assembly 378 to cooperate in accumulating air under pressure and suddenly releasing it for purging operations in a fast flow with a snap action.

To control the accumulation of air and its release, the purge valve assembly 352 includes a purge valve element 362, a retainer plate 366, a retainer nut 368, a spring 370, a bottom plate 372 and a rolling diaphragm 364. The bottom plate 372 is mounted to the housing 386 by the screws 374A and 374B which pass through the bottom plate and washers 376A and 376B, being threaded into the tapped holes 412A and 412B in the valve seat plate 354 to hold the purge valve element 362, retainer plate 366, retainer nut 368 and rolling diaphragm 364 in place to operate cooperatively with the valve seat plate 354 within the accumulator assembly 356. The rolling diaphragm is a member that when depressed unrolls loose material rather than only stretching and thus can be moved further.

With this arrangement, as air pressure builds within the chamber 422, pressure moves the purge valve element 362 downwardly, causing the air to exert further force on the rolling diaphragm 364 to increase the force rapidly. This increased force causes the valve to open fully to permit the rapid escape of air through the outlet assembly 378 by rapidly forcing the spring 370 downwardly to unblock the outlet assembly 378.

The outlet assembly 378 includes a purge air line or tubing 382, a port assembly 380, and an air pressure sensing outlet 384. The outlet 384 communicates with a line to be described hereinafter to supply air pressure to a pressure sensor that generates signals for the central controller. The air line or tubing 382 communicates with the port assembly 380 and with the bubbler line 132 (FIGS. 3 and 5) to supply air under pressure rapidly during a purge operation.

In FIGS. 7, 8 and 9, there are shown an elevational view, a top view and a developed view of the bracket 388 respectively. As shown best in FIG. 7, the bracket 388 includes a top portion 414 and a bottom portion 416. The top portion includes slots such as 404A to receive a corresponding machine screw such as 406A (FIG. 6). The three openings 408A-408C extend vertically through both the top portion 414 and the bottom portion 416, serving to hold the bracket around the housing 386 (FIG. 6) for mounting purposes and to provide a means for fastening to the gate housing 74 (FIG. 3).

As best shown in FIG. 8 and 9, the bracket is formed by stamping an elongated plate from stainless steel, resulting in an integrally formed member with the slots 404A and 404B positioned to be on opposite sides of the housing 386, openings 408A-408C extending downwardly on one edge of the portion 416 and the openings 418A and 418B aligning with the openings 408A and 408B on the opposite edge of the portion 414 so that when bent as shown in FIG. 8, the openings 408A and 408B are aligned respectively with the openings 418A and 418B and a loop is formed to fit around the housing 386 (FIG. 6).

In FIG. 10, there is shown an elevational view, partly-broken-away, partly exploded and partly sectioned of the bubbler purge system 350 with the broken away and sectioned portion having a valve seat outlet rotated 90 degrees about a vertical axis so that it shows in the sectioned portion. This purge system has an accumulator assembly 356, a purge valve assembly 352, and the outlet assembly 378 exploded to a greater degree than that shown in FIG. 6 and being a right elevational view rather than a front elevational view as is the case with FIG. 6.

As shown in FIG. 10, the accumulator assembly 356 includes the valve seat plate 354, the inlet 410, and the compartment 422. These parts cooperate as explained in connection with FIG. 6 so that, when the air pressure builds in the compartment 422 to a predetermined level, the purge valve assembly snaps open and releases air through the outlet assembly for a purging operation.

For this purpose, the valve seat plate 354 includes a valve seat 358, a valve guide 426, the air holes 430A and 430B, an annular valve chamber 436, and a valve seat outlet port 454. These parts are positioned so that the valve seat receives the purge valve assembly 352 in one position to seal the outlet assembly and in another position to open the outlet assembly.

For the purpose of this cooperation, the purge valve assembly 352 includes an O-ring 424, the purge valve element 362, the rolling diaphragm 364, the retainer plate 366, the retainer nut 368, the spring 370 and the bottom plate 372. These units are mounted to the housing by the machine screws 374A and 374B and the corresponding washers 376A and 376B which pass through openings in the end plate and into holes such as shown at 412A and 412B (FIG. 6) in the valve seat plate 354.

The O-ring 424 is compressed between a portion of the valve seat 358 and a top surface of the purge valve element 362, forming a seal against the flow of air from the accumulator compartment 422 through valve seat outlet port 454 to the outlet assembly 378. This outlet communicates with the annular chamber 436 to receive air therefrom and permits the flow of air through the outlet assembly 378 when the O-ring 424 is released by the depression of the spring 370.

The downwardly extending cylindrical valve guide 426 fits through an opening 428 in the purge valve element 362, which opening extends downwardly to a closed end. With this arrangement, the valve element 362 is kept aligned as it moves upwardly and downwardly under the control of the air pressure within the compartment 422 and of the force of the spring 370.

To close and open the valve seat outlet port 454, the purge valve element 362 includes an inner portion 432 inside the O-ring 424 and an outer portion 434 outside the O-ring within the rim of the purge valve element 362 and recessed in its flat inner surface. It includes stepped cylindrical bosses, one of which is externally threaded, and both of which fit within an opening in the retainer plate 366 to be held thereto by the nut 368. The the rolling diaphragm 364 is held between the valve element 362 and the retainer plate and extends beyond them to engage the top annular end of upwardly extending walls on the bottom plate 372. The nut 368 is threaded on the shoulder to hold the rolling diaphragm 364 in place, with the helical spring 370 fitting around the shoulder of the element 362 and abutting the bottom plate 372.

The outlet assembly 378 includes the port assembly 380, the purge air line 382 and the air pressure sensing outlet 384, with the air sensing outlet 384 extending through the outlet housing for connection to a sensing line 392 (FIG. 5). The port assembly 554 includes an outer spout connection 385 for engaging the purge air line 382 that eventually connects to the bubbler 132 (FIGS. 1-5) through tee connector 390 (FIGS. 3 and 5).

The port assembly 380 includes the check valve housing 440, an O-ring 442, a check valve 444 and a tank outlet housing 446. With this arrangement, the check valve 444 includes a small opening 544 (FIG. 25) for the bleeding of air. This is intended to maintain the pressure at the pressure of the bubbler line or atmospheric pressure to establish a standard pressure for the setting of the spring. The check valve is set at a low force to prevent premature loss of pressure before the valve opens. It receives air from the compartment 422 through its inlet port 524 and when open permits it to escape through openings 546A-546C between inner wall members 532 into the outlet housing 446 and from there to the purge air line 382 and the sensing connection 384.

FIGS. 11-14 are a bottom view, front elevational view, and two diametrecal transverse sections respectively of the generally cylindrical valve seat plate 354 having, as best shown in FIG. 11, an annular recess 458, a cylindrical downwardly extending valve guide 426, holes 430A and 430B, a downwardly extending annular sealing cylindrical wall 456 of the valve seat 358, an annular recessed valve chamber 436, a downwardly extending cylindrical rim 460 and a valve seat outlet 454. The valve guide 426 is cylindrical and extends downwardly from the center of the valve seat within the central recess 458 which has a circular cross-section.

The two holes 430A and 430B are on either side of the guide 426 and as best shown in FIG. 13, extend all the way through the plate adjacent to the post 426 within the recess 458 to permit the passage of air from the compartment 422 (FIG. 10) into the space formed by the recess 458 to exert downward pressure on the inner area surrounding the guidepost 426 on the purge valve assembly 352.

The recess 436 is sealed from the holes 430A and 430B and the compartment 422 by the engagement of the O-ring 424 (FIG. 10) with the downwardly extending wall or annular sealing ring 456 of the valve seat 358 when the purge valve assembly 352 is closed and exerts a pressure equal to the pressure in the compartment 422. Thus, the pressure results in exerts a force against the spring. 370 (FIG. 10) equal to the area of the valve element 362 that seals the recess 458. This area is referred to from time to time as the purge valve inner area.

As best shown in the sectional views of FIGS. 13 and 14, the openings 430A and 430B (FIG. 13) connect the compartment 422 to the inner area defined by the inside of the O-ring 424 (FIG. 10) but provide the annular recess 458 which fills with air from the compartment 422 (FIG. 10) at the same pressure as the compartment 422 and exerts pressure against the valve, tending to open the valve. The inner area is sufficiently large so that at the design pressure provided by the reservoir, the valve opens slightly to break the seal between the O-ring and the annular sealing ring 456 of the valve seat 358 so that air flows therebetween.

As soon as air starts flowing beyond the annular ring 456 of the valve seat 358 into the recess 436 forming the annular valve chamber, the total force against the spring 370 is rapidly increased because the area receiving the same pressure as the compartment 422 increases. Since this pressure is the same as in the compartment 422 and the area is much large, the spring 470 is quickly overwhelmed and the valve snaps open.

As best shown in the elevational view of FIG. 12, the valve seat outlet port 454 opens into the annular valve chamber to release air to the outlet in a fast flow from the compartment 422. This onrush of air is with high volume because the valve is now fully opened so that the valve serves as a snap-open switch, which when a threshold pressure is reached, moves quickly to a full open condition under the control of only hydraulic and mechanical forces. The opening is related to a ratio of two hydraulic forces moved by substantially the same hydraulic pressure which overcomes a biasing means (the spring 470).

In FIGS. 15 and 16, there is shown a bottom and transverse sectional view, respectively, of the purge valve element 362 having a downwardly extending spring engaging boss 462 in its center with an upwardly opening guide hole 428 through it, a spring-receiving annular groove 464, a cylindrical externally threaded portion 466, an upwardly opening O-ring groove 468 and a plate-receiving annular recess 500. The valve element is adapted to move within a limited range of motion under the control of a small space between the end cap 372 (FIG. 10) and the valve seat plate 354 under the control of air pressure from the compartment 422 (FIG. 10) and the spring 370 (FIG. 10).

The movement of the valve element 362 is sufficient to compress the O-ring 424 against the annular sealing ring 456 in the valve seat 358 of the valve seat plate 354 to prevent air from passing O-ring 424 and through the outlet port 454 (FIG. 12) in one position or to move down to another position a sufficient distance to snap open and permit high velocity air to go through the outlet port 454 into the outlet assembly 380 (FIG. 10) for a purging operation.

To provide the closing and opening operation for air utilized in the purging operation, the spring engaging boss 462 fits within the spring 370 (FIG. 10) and the top portion of the spring 370 is received by the spring-receiving annular groove 464 to be held therein and exert upward force against the force of air in the compartment 422 (FIG. 10). The range of motion is controlled by the distance between the spring receiving boss 462 and the end cap 372.

As the valve element moves, the O-ring which normally resides in the O-ring groove 468 is loosened or tightened against the valve seat 358 to either permit the escape of air or prevent the escape of air from the compartment 422, with the plate receiving annular recess 500 receiving or moving from the downwardly extending portions of the valve seat plate 354.

In FIG. 17, there is shown a plan view of the diaphragm 364 having a circular member 502, a centrally located opening 504, and side openings 506A and 506B. The side openings 506A and 506B are adapted in size to permit the bolts 374A and 374B to pass therethrough into the valve seat plate 354 (FIG. 6) without preventing the inner portions of the diaphragm 502 to move a short distance. The centrally located opening 504 fits around the cylindrical threaded portion 466 of the purge valve element 362 so that the diaphragm cooperates with and is held to the valve element 362 by the retainer plate 366 and nut 368 to form a larger diameter impediment to air flow, that diameter extending throughout the inner diameter of the housing 386 to increase the area for air passing through the openings 430A and 430B (FIG. 10).

In FIGS. 18 and 19, there are shown a plan view and a side view of the retainer plate 366 having a circular diameter conforming to the diameter of the valve element 362, a central opening 363 which fits over the threaded portion 466 of the purge valve element 362 (FIGS. 15 and 15) and a downwardly extending flange 365 forming a cylindrical recess that receives the nut 368 for threading against the threaded portion 466 of the purge valve element 362, so that when threaded onto the element 363, the diaphragm 364 is held in place for movement with the valve element 362 and is capable of embarking force to the valve element caused by air escaping the compartment 422. Although a diaphragm has been described in the preferred embodiment to prevent the escape of air, any other suitable movable seal may be used such as a piston of or bellows or the like in a manner known in the art.

In FIGS. 20 and 21, there is shown a plan view and a top view taken through section 21—21 of FIG. 20, respectively, having a circular bottom plate with an annular end flange 508, a central air hole 450, holes 438A and 438B for receiving the bolts 374A and 374B (FIGS. 6 and 10) for holding the bottom plate to the housing and upwardly extending annular wall portions 510, so that the bolts 374A and 374B hold the bottom plate 372 with the annular wall portions 510 abutting against the downwardly extending cylindrical rim 460 (FIG. 13) and holding the circular member 502 (FIG. 17) of diaphragm 364 between them.

With this arrangement, the upwardly extending walls enclose the purge valve element 362, the O-ring 424, the diapragm 364, the retainer plate 368, the retainer plate 366, the retainer plate nut 368 and the spring 370. The valve element 362 is permitted to move slightly within the bottom plate 372 to open a path for air through the outlet 378 and close that path in such a way to provide sudden bursts of purging air to the bubbler 132.

In FIGS. 22 and 23, there is a shown an elevational view and a transverse section view through lines 23—23, respectively, of the check valve housing 440 having an air opening 512, an externally threaded connecting tube 514, a check valve housing chamber wall 516, an O-ring annular groove 518, a shoulder 520 and an externally threaded cylindrical outlet connection portion 522. The check valve housing 440 is intended to receive the check valve 444 (FIG. 10) within the check valve housing chamber wall 516 to be threaded into the valve seat outlet 454 (FIG. 10) to receive air from the chamber when the valve assembly 352 is open and to be connected by the externally threaded outlet connection 522 to the tank outlet housing 446. The O-ring groove 518 receives the O-ring 442 to provide a sealing connection between the chamber wall and the check valve 444.

In FIGS. 24 and 25, there is shown an elevational view and a sectional view taken through lines 25—25 of FIG. 24 of the check valve 444 respectively, having an inlet opening 524, outlet openings 546A–546C, an outer housing 526, an inner housing 532 and a spring-loaded valve assembly within the inner housing 532. The outer wall 536 includes an inwardly extending annular flange 539 having an edge 530 abutting the spring-loaded valve. The inner housing includes annular insulation 542 that forms when a seal is between the outer and inner housings and, when the valve is closed, a seal is between the spring-loaded valve and the inner housing.

The spring-loaded valve includes a helical compression spring 534, a shaft 538, an air blocking face 540 and an air opening 544. The shaft 538 fits within a shaft opening 536 aligned in the inner and outer housings and the outlets 546A–546C pass through both the inner and outer housing.

With this arrangement, air pressure from the outlet 454 (FIG. 10) causes communication between the compartment 422 and the opening 524 to exert pressure against the air blocking portion 540 except for a slight equalizing trickle of pressure through the opening 544. When the purge valve 352 (FIG. 10) is opened, the increased pressure forces the shaft 538 further through the opening 536 against the pressure of the spring 534 to permit air to escape around the face 540 after it clears the sealing material 542 and permits it to pass through the openings 546A–546C. Thus an onrush of air passes through the ring of openings 546A–546C into the bubbler through the outlet 446 into the bubbler 132.

In FIGS. 26 and 27, there is shown a right elevational view and a transverse sectional view of the tank outlet housing 446 having internally-threaded connection walls 550, inwardly sloping outer walls 552, a connecting wall for the purge air line 382 (FIG. 10) that leads to the bubbler 132 and an outlet 558 for the purge air line 382. The connecting walls 550 are threaded on the externally-threaded walls 522 of the checkvalve housing so that air from the check valve flows in through the sloping walls 522 through the outlet 556 into the air pressure sensing outlet 384 (FIG. 10) and through the outlet 558 to the purge air line 382 which leads to the bubbler 132. Some air flows through the outlet 556 into the air sensing port 384 (FIG. 10) to provide pressure information.

The air hole 544 may provide a path to air that reduces the pressure between the purge valve assembly 352 in embodiments to be used at deep locations to equalize the pressure at the outlet and lower portion of the purge valve. This path is completed through a connection 383 (FIG. 5) from the sensing outlet 556 to lines 383 and 251. This pressure may be at either the bubbler in some embodiments or atmosphere in other embodiments so as to maintain a pressure differential referenced to a fixed standard to control the opening of the purge valve assembly 352.

In operation, air is supplied to purge tank 350 from reservoir 312 (FIG. 5) or by pump 402 (FIG. 5) in remote section 14 (FIG. 1) through air line 398 (FIG. 5). The air enters the accumulator assembly 356 of purge tank 350 through inlet 410. The air in accumulator assembly 356 remains at the same pressure as the air in the reservoir 312 as long as O-ring 424 is seated against valve seat 358 which is part of valve seat plate 354. The spring 370 provides the force on purge valve assembly 352 to seal O-ring 424 against valve seat 358 thus stopping air from flowing out of accumulator assembly 356. The rolling diaphragm 364 is retained between valve seat plate 354 and tank bottom plate 372 with screws 374A and 374G and washers 376A and 376B.

The accumulator assembly 356 supplies air through holes 430A and 430B (FIG. 13) to inner portion 432 (see FIG. 10) of purge valve assembly 352. The inner portion 432 of purge valve assembly 352 is defined by the location of O-ring 424 against valve seat 358. The outer portion 434 of the purge valve is considered to be that area of the purge valve assembly 352 external to the circular location of O-ring 424 against valve seat 358 inclusive of the area of the rolling diaphragm 364 which will also apply force to the valve when air pressure is encountered.

Air does not flow out of the accumulator assembly 356 through holes 430A and 430B unless the air pressure in accumulator assembly 356 times the cross sectional area of the inner portion 432 of valve is equal or greater than the force of spring 370. When the air pressure is sufficient to overcome spring 370, air will proceed to flow into valve chamber 436. Since the air cannot flow by valve assembly 352 which has rolling diaphragm 364 sandwiched between the valve seat plate 354 and tank bottom plate 372, the air can only proceed through valve chamber 436 to the purge tank outlet assembly 378. The hole 458 in tank bottom plate 372 vents the backside of rolling diaphragm 364 to atmosphere in the preferred embodiment and to the bubbler pressure in other embodiments to provide a reference pressure for the actuation of the purge valve switch.

The purge tank outlet assembly 378 includes check valve housing 440, O-ring 442, check valve 444, and tank outlet 446. Check valve 444 is installed into check valve housing 440 with O-ring 442 to eliminate unwanted air leakage. Check valve 444 has a small hole 544 (FIG. 25) drilled in it to provide a slow controlled leak.

To perform a purge cycle, the accumulator assembly 356 is maintained at essentially the same air pressure as an air reservoir 312 in remote station 14 or 14A (FIGS. 1 and 5). The remote station turns on its air pump thus increasing the air pressure in its reservoir 312 and in accumulator assembly 356. Air pressure builds in accumulator assembly 356 until pressure on inner portion 432 of purge valve assembly 352 starts to overcome the force from spring 370. As the valve element the purge valve assembly starts to open, air flows through holes 430A and 430B in valve seat plate 354 through the interface between O-ring 424 and valve seat 358 and then into valve chamber 436. Some air flows through hole 544 in check valve 444 but less than that is flowing by the interface between O-ring 424 and valve seat 358.

Because the pressure begins to rise in valve chamber 436 from the air flowing past the O-ring, the force due to air pressure on inner portion 432 times its cross sectional area plus the air pressure on the outer portion 434 times its cross sectional area is sufficient to fully open purge valve assembly 352. Once the purge valve assembly 352 is open, air flows rapidly through holes 430A and 430B in valve seat plate 354 into valve chamber 436. The increased pressure in chamber 436 causes check valve 444 to quickly open thus completing the air path that allows air to rush through holes 430A and 430B into chamber 436 through check valve 444, down through bubbler tube 132 and out bubbler outlet 134 (FIG. 2). This rush of air sweeps away particles or growth in the bubbler tube and its outlet.

As air rushes out bubbler tube 132, pressure drops in accumulator assembly 356 and in valve chamber 436. When the air pressure has decreased so that air pressure in valve chamber 436 times cross sectional area of outer portion 434 plus air pressure in accumulator assembly 356 times the inner portion 432 approaches spring force, the valve starts to close. The purge valve assembly 352 fully closes as air pressure continues to drop. Pressure in the valve chamber 436 continues to drop after the purge valve assembly 352 has closed since check valve 444 closes at a lower pressure. Pressure in valve chamber 436 continues to drop rapidly until check valve 444 closes, at which time the air pressure drops more slowly as air flows out hole 544 in check valve 444.

If air is no longer flowing from reservoir 312 to accumulator assembly 356, the pressure in valve chamber 436 drops to that in bubbler tube 132. If air is still flowing into accumulator assembly 356, purge valve assembly 352 may cycle again before pressure in valve chamber 436 drops to that pressure in bubbler 132. Since there may be some residual pressure on the outer portion 434 of purge valve assembly 352, the valve may open at a somewhat lower pressure. If the controller 312 continues to supply air, purge tank 386 continues to cycle, providing quick bursts of air whenever the air pressure in accumulator assembly 356 builds sufficiently to trip purge valve assembly 352.

The components may be sized for the desired results. In the preferred embodiment, the desired pressure in accumulator assembly 356 to open purge valve assembly 352 is between 5 ½ psi and 8 ½ psi. This range permits the controller to perform other functions using the same air reservoir without triggering a purge operation. However in other embodiments, the range may be narrower and the values may be selected together with the size of the inner and outer areas of the valve element and the resistance of the spring in accordance with the depth that is to be used.

This is accomplished by selecting an O-ring and O-ring groove that results in an effective pressure diameter of about 0.83 inches. The effective cross-section for inner portion 432 is about 0.55 SI (square inches). A spring with a spring rate of about 15 lb/in that is compressed about 0.28 inches in the closed position is selected. This selection allows the purge tank to typically dump air at pressures between 7 and 8 PSI. These components could be easily changed to achieve different flow pressures.

The cross sectional area of outer portion 434 of purge valve assembly 352 is about 1.3 SI based on the effective cross sectional pressure area of rolling diaphragm 364 less inner portion 432. The total of inner portion 432 and outer portion 434 is about 1.84 SI. The purge valve should thus close at about 2 ¼ PSI. The ratio between opening and closing is about 3 to 1. This ratio can be varied according to the desired effect.

The down stream check valve 444 has a ½ PSI to a 1 PSI crack pressure. At slightly higher pressures, the valve allows air to flow quite freely. By restricting flow until pressures of at least ½ PSI builds up in valve chamber 436, the total force on the purge valve assembly 352 is sufficient to allow the purge valve to fully open. It is important that the pressure to open and to close valve 444 is less than it takes to close purge valve 352. If not, check valve 444 closes before purge valve assembly 352. This traps air pressure on outer portion 434 which along with pressure on inner portion 432 keeps purge valve assembly 352 open. Check valve 444 then appears more like a regulator with a more constant flow of air instead of bursts.

The hole 544 in the check valve 444 is 0.012 diameter. This is sized small enough to restrict the flow of air out hole 544 to less than that flowing in tank inlet 410 taking line losses in air line 398 and pumping capacity in controller 10 into consideration. Hole 544 may be downsized to as small or even smaller than 0.008 if line 398 reaches lengths in excess of several hundred feet. However, if hole 544 becomes too small, the pressure in valve chamber 436 will not drop quickly. The additional pressure on the outer portion 434 will cause the purge valve assembly 352 to open at a lower pressure.

The hole 544 in the check valve 444 communicates pressure at the bubbler outlet into valve chamber 436. If the bubbler outlet 134 (FIG. 3) is sensing high heads of pressure, this pressure has a pressure effect on outer portion 434 because of the air leakage through the hole 544 in the check valve. Thus, the spring 370 must apply more force at deeper depths. In a system that encounters a wide range of pressures at the bubbler outlet, the outer portion should have a cross section less than the inner portion so that it is less sensitive to the pressure variations.

The pressure in the accumulator or equivalent structure in embodiments of the valve used in some other applications such as for controlling bladder pump inflation and deflation, may have pressures of between 5 to 300 psi. In purge valves for bubblers, the pressure in the accumulator 422 may be between 1 and 30 psi. The force exerted by the spring 470 in such applications must also be in range of the force of the pressure multiplied by the area for triggering the valve. The accumulator and the conduits should provide a flow rate to the bubbler port that is at least one cubic inch per second. The actually required flow rate will depend on the size of the bubbler conduit and port.

In operation, the remote station 14 and the flowstream local station 12 are brought to a site, such as a manhole or the like. The air and electrical conduits are connected, the bladder 80 (FIG. 2) is deflated and the flow housing 60 (FIG. 2) is inserted into the pipe 46 (FIG. 2). The bladder is then inflated to grip the inside of the pipe 46 (FIG. 2) and the adjustable mounting unit 44 (FIG. 2 and FIGS. 5–8) is then adjusted or leveled.

To level the local station along its right to left axis, the clamping plates 140 and 142 are pivoted so that they hold the gate housing 74 horizontally with the end of the pipe housing abutting the outer plates or being adjacent thereto but leaving sufficient room for their adjustment. Leveling is accomplished by turning the bolt 240 (FIG. 8) or its counterpart on the opposite side while holding the unit so that the bubble is aligned along its right to left centerline. The wing nuts 234 are then tightened.

To level the local station along its front to back axis, screws 150A–150D (FIG. 3) are loosened and the housing lifted until the bubble level 156 (FIG. 3) indicates that the flow path is level. The screws 150A–150D are then tightened. The bladder 80 may be further inflated by pumping air through the tube 82 (FIG. 2) to seal against the flow and the leveling process repeated. It is desirable to check the bubbler level 156 and readjust the flow bed if it is now off-center.

The bubbler may be periodically corrected for drift by incorporating an electrically-controlled valve in the line to: (1) close the line to water; (2) open the portion of the line communicating with the high pressure side of the pressure-to-electrical transducer to atmosphere while the low pressure side is at atmospheric pressure to develop a zero signal for calibration; and (3) to connect the high pressure side of the transducer to atmosphere through the valve 316. A check valve may be used to prevent the air from flowing from the bladder 80 back to the reservoir (FIG. 10) and prevent the inflow of water as it depressurizes.

In the preferred embodiment, a look-up table has been constructed which correlates gate position and depth upstream of the gate (head of pressure) with the flow rate. This table has been constructed by adjusting the gate and making measurements using a weigh tank and timer to arrive at values corresponding to different positions of the gate and different depths of head. This look-up table is used by the controller to provide data concerning the flow rate in response to received signals from the gate sensing system 20 and depth sensing system 24. These coordinates are used in a well known manner to access data in the look-up table and provide a flow rate. Other look-up tables with greater accuracy or less accuracy or for modifications of the equipment can be constructed in a similar manner.

Once the look-up table is in place, the equipment can be operated in a number of modes to obtain flow measurement and to provide a simulated stilling well for drawing samples. In its operation, some benefits are obtained by maintaining a clean, flushed flow path and this can be conveniently automatically accomplished, if desired. For this purpose, the gate assembly 62 is periodically closed, a head of liquid created and then opened. The onrush of fluid clears the flow bed for the benefit of a bubbler port 24 (FIGS. 1–4) or for the sample port at 26.

The flow meter may operate in any of several modes, for example, the gate may be moved to maintain a predetermined constant head and the look-up table may utilize gate position at the predetermined head to determine flow rate. To accommodate many different flow rates, several such positions can be selected, each of which has a look-up table.

In an alternative mode of measurement, the gate may select incremental positions such as fully open in which equations for fully opened conduits can be used, or it can assume incremental positions appropriate for the flow rate to maintain a head within the dynamic range of the measuring instruments and a look-up table can be used for that position and different depths, or for example, the gate may be changed in position and the rate of change of head and increase in head may be correlated with flow rate.

Another method of flushing and then measuring flows using a look up table is to fully close the gate to reduce flow to near zero. The upstream conduit will begin to fill, thus increasing the head. At a predetermined first head, the gate opens and flushes the line at velocities that can support a large amount of solids. As the conduit is flushed, the head drops. At a second predetermined head, the gate again closes to reduce flow to zero and refill the conduit. Such a method consumes more power in positioning the gate, but is more effective in especially low flow conduits that have excessive solids.

In this method of flow monitoring, the gate may be fully closed or almost closed while filling the conduit. When flushing and lowering the head, the ideal gate position is slightly into the flow stream although it may be also lifted out of the flow stream. The measurements of gate position and depth are at sufficiently frequent intervals and the look up table sufficiently detailed so that the readings during the closed gate and open gate positions can be plotted and measurements of flow rate that are not distorted by such fluctuation used or the time period of averaging can be selected to be large enough to average out the zero flow to high flow fluctuations.

The different modes of operation are each possible because, closing the gate assembly 62 relative to the flow path, causes the flow to "back-up" and the level of the liquid behind the multiple position gate assembly 62 to increase at a rate related to rate of flow of the fluid. Similarly, the raising of the gate opens the flow path and reduces its cross sectional blocking area, increasing the cross section of flow, causing the level of fluid to decrease at a flow rate related to the rate of flow of liquid in the pipe. Similarly, if the gate is moved to a fixed position and maintained in that position, the head stabilizes at a level related to the flow of fluid in the pipe 46. All of these factors may be utilized in determining the flow rate.

To move the multiple position gate assembly 62 in a direction which reduces the flow cross section, air is pumped into the chamber above the piston 106 causing it to move downwardly and stabilize at a location where the spring 108 and forces of upstream liquid counteract the pressure. Similarly, when the gate assembly 62 is to be opened, air is removed causing the spring 108 to move the piston 106 upwardly and thus moves the rod 102 upwardly. Any movement is sensed by the LVDT and the movement and new location are transmitted to the remote unit which may be used for correction of the location of the gate in some modes and/or directly calculate flow rate in other modes.

There are several modes available for cooperation between the sampler and the electronics and air portions of the controller at the remote station. For example, sampling may be performed periodically in units of time. As the units pass, the gate assembly 62 may be closed to back up the liquid so that the depth at which sampling occurs is increased sufficiently for a sample which is above the inlet port for the entire time of sampling and the sample is thus more representative. A flush cycle may be performed before sampling, if desirable. In another mode related to flow, flow rate may be determined and timed and when a predetermined amount of volume of liquid has passed, the gate may close to raise the volume to a sufficient height for an accurate sample.

In a sequence using the purge system, the step 476 reads the gate position and is followed by a read liquid level step 478 which is followed by a control gate step 480 and a calculate flow step 482. The calculate flow step 482 is followed by a decision 484 to determine if two seconds have elapsed. If they have, the step to increment the flow totalizer is performed at 486; otherwise, the step of forming the plotter image is performed at 488.

After forming the plotter image, a decision is made as to the priority sequence two at decision step 490. If it is a priority sequence two involving the bubbler, a gate flush is performed at step 492. If it is not, then the time is checked again at step 485. If it has not, the program returns to the timing step and repeats it.

If the time has elapsed, the program checks on the last clearing step at step 487. If the last clearing step was a purge step shown 489, than the clearing step is performed at the super bubble step 494 by increasing the pressure through the bubbler. If the last clearing step was not a purge step, than the purge step is performed. After clearing the bubbler, the program proceeds to another sequence not involving the purging of the bubbler and described in the aforementioned patent application to Carson et al.

Because the valve is able to automatically release fluid and accumulate fluid at periods of time related to the pressure setting of the biasing member and the pumping rate of fluid into the accumulator, it has been proposed that the valve may be used for other purposes such as to control the cycling of a bladder pump of the type that repetitively inflates and deflates a bladder to change the volume of a pumping chamber and thus pump fluid.

From the above summary, it can be understood that the novel method and apparatus of this invention has several advantages, such as for example: (1) it is relatively simple, inexpensive and easy to use; (2) it permits relatively precise depth measurements, even in flow streams carrying material capable of blocking a bubbler outlet port; (3) it is capable of cooperating with a versatile apparatus that can be used both to measure flow rates and take samples in a wide variety of streams and at a wide variety of different depths of flow and flow rates; (4) it is capable of great precision under difficult measuring conditions; (5) the apparatus can be used to perform a number of different measuring methods; (6) the valve can be used without electrical connection at the valve itself; and (7) it permits high-volumetric-rate air purging operations using a source near the bubbler outlet port without electrical connection.

Although a preferred embodiment has been described with some particularily, many modifications in variations are possible in the preferred embodiment without deviating from the invention. Therefore, it is to be understood that, within the scope of the appended claims, the invention may be practiced other than as specifically described.

APPENDIX A

```
/***********************************************/
void get_head()              /* Read head */

{
int temp_head;

char inbit();
int inword();

if(sb_time>3 && az_step==0 && post_pump_delay==0)
    {
        temp_head=read_head() - zero_offset + TUBING_OFFSET +
            bubbler_offset;
        if(sb_time>60 || temp_head < (head+50) || temp_head >
            last_head)
            head=temp_head;
        last_head=temp_head;
    }
else last_head=6000;

head_total+=head;
head_count++;
head_total2+=head;
```

```c
head_count2++;
head_total3+=head;
head_count3++;
if(menu_number==20 && lvdt_disp==2)
    {
    if(head_avg_control==2) temp_head=avg_head;
    else temp_head=head;
    if(head_inch_flag)
        sprintf(s,"%6.3f",(float)(temp_head-120)/200.0);
    else
        {
        Scopy(S,135);
        sprintf(s,S,temp_head);
        }
    sdisplay(33,s);
    }
if(lvdt_count<20 &&
   (head>(11*lvdt_head/10) || head<(9*lvdt_head/10)))
    lvdt_count=20;
}

/****************************************************************/
int read_head()

{
int x;
int zero_head;

char inbit();
int inword();
void outbit();

a_d_to=0;
outbit(port5a,7,1);
while(inbit(port6b,5))
    if(a_d_to>=3) return(head + zero_offset);
x=inword(port4);
zero_head=x & maska;
if(~x & maskpol) zero_head=-zero_head;
return(zero_head);
}
/****************************************************************/
void auto_zero()
{
int diff;
int new_az_value;

void outbit();
int read_head();

if(auto_zero_control==1 && manual_zero_flag!=1) az_step=5;
mode_letter=0x41;
if(az_step==0) az_step=1;

switch(az_step)
```

```c
{
case 1:
    outbit(port5b,4,1);
    auto_zero_time=120;
    az_step=2;
    az_delay=0;
    az_count=0;
    break;

case 2:
    if(auto_zero_time==0) az_step=3;
    if(az_delay==0)
        {
        new_az_value=read_head();
        diff=new_az_value-old_az_value;
        if(diff<0) diff=-diff;
        if(diff<3) az_step=3;
        old_az_value=new_az_value;
        az_delay=5;
        offset=0;
        }
    break;

case 3:
    if(az_delay==0)
        {
        offset+=read_head();
        az_delay=1;
        az_count++;
        if(az_count>=16) az_step=4;
        }
    break;

case 4:
    offset+=8;
    zero_offset=offset / 16;
    az_step=5;
    diff=zero_offset-old_offset_val;
    if(diff<0) diff=-diff;
    if(diff>10) auto_zero_time=300;
    else if(diff>=6) auto_zero_time=600;
        else if( diff<3) auto_zero_time=old_az_time * 2;
            else auto_zero_time=old_az_time;
    if(auto_zero_time>3600) auto_zero_time=3600;
    else if(auto_zero_time<300) auto_zero_time=300;
    old_az_time=auto_zero_time;
    old_offset_val=zero_offset;
    break;

case 5:
    outbit(port5b,4,0);
    az_delay=5;
    az_step++;
    break;
```

```c
        case 6:
            if(az_delay==0)
                az_step++;
            break;

default:
            az_delay=10;
            prior_req=0;
            manual_zero_flag=2;
            az_step=0;
            break;
            }
}
/*************************************************************/
int calc_av_head()
{
int av_head;

av_head=head_total / head_count;
/*sprintf(s,"%4d",av_head);
sdisplay(20,s);*/
head_total=0;
head_count=0;
return(av_head);
}
/*************************************************************/
int calc_av_head2()

{
int av_head2;

av_head2=head_total2 / head_count2;
head_total2=0;
head_count2=0;
/*sprintf(s,"%4d",av_head2);
sdisplay(14,s);*/
return(av_head2);
}
/*************************************************************/
void super_bubble()
{ if(sb_time<4 || extra_sb_pressure>5) mode_letter=0x50;

switch(sb_freq)
    { case 2:
        sb_freq_sec=300;
        break;

case 3:
        sb_freq_sec=600;
        break;
```

```
        case 4:
            sb_freq_sec=900;
            break;

case 5:
            sb_freq_sec=1800;
            break;

default:
            sb_freq_sec=3600;
            break;
        } if(man_purge)
    {
    if(sb_control != 1) sb_time=0;
    sb_pulse_time=cable_len * 30;
    man_purge=off;
    } if(extra_sb_pressure>30) extra_sb_pressure=4;

if(((sb_freq!=1 || purge_step>14) && sb_time > sb_freq_sec &&
    sb_control != 1) || extra_sb_pressure>5)
    {
    if(extra_sb_pressure < 5)
        {
        extra_sb_pressure++;
        if(sb_control != 1) sb_time-=sb_freq_sec;
        sb_pulse_time=(cable_len + 1) * 50;
        }
    else if(extra_sb_pressure == 5)
        extra_sb_pressure=6;
    else if(super_belch_control != 1 &&
        ((extra_sb_pressure > 20  &&  cable_len<5)   ||
(extra_sb_pressure>25)))
        {
            extra_sb_pressure=4;
            if(sb_control   != 1   &&   sb_time>sb_freq_sec)
    sb_time-=sb_freq_sec;
            post_pump_delay2=5;
        }
    else if(super_belch_control == 1 && extra_sb_pressure >
14)
        {
            extra_sb_pressure=0;
            if(sb_control   != 1   &&   sb_time>sb_freq_sec)
    sb_time-=sb_freq_sec;
            sb_pulse_time=(cable_len + 1) * 75;
        }
    }
    else if(head>sb_head && az_delay==0 && sb_control != 1)
        {
        if(++sb_head_count>10 && sb_rise_time>5)
            {
            if(head>sb_start_head)
```

```
            {
            sb_pulse_time=2 * cable_len;
            sb_head_count=0;
            sb_time=0;
            if(gate_control_time2 > 3)
                    {
                    gate_control_time1=1;
                    gate_control_time2=3;
                    }
            }
        else
            {
            sb_rise_time=0;
            sb_start_head=head+300;
            }
        }
    }
    else
        {
        sb_head_count=0;
        sb_rise_time=0;
        sb_start_head=head+300;
        } sb_head=head;
}
```

What is claimed is:

1. A method of maintaining constant back pressure in a flow line comprising the steps of:

pumping fluid into a first reservoir;

repetitively causing a self-activated flow of fluid under pressure into the flow line through a restrictor from the first reservoir to cause bubbling through a liquid;

pumping the fluid into a second reservoir serving as an accumulator at a first volumetric rate, wherein pressure in the accumulator is increased;

opening a pressure-actuated release valve in the accumulator when a predetermined pressure is reached; and rapidly allowing a burst of the fluid at a substantial pressure and velocity to flow from the accumulator through the line, wherein the pressure in the accumulator is reduced;

closing the pressure-actuated release valve; and continuing to pump the fluid into the accumulator wherein a cycle is repeated at intervals related to the rate of pumping of fluid into the accumulator.

2. A method according to claim 1 wherein the fluid is air and the air is caused to flow to an orifice of a bubbler.

3. A method according to claim 1 in which the step of opening a release valve in the accumulator when a predetermined pressure is reached comprises the substeps of:

accumulating air in the accumulator until the pressure in the accumulator against the effective area of the inner portion of a release valve element overcomes the resisting force of a spring, wherein the valve element moves slightly, permitting air to flow over a larger area of the valve element; and increasing the area receiving the accumulator air pressure to include an outer portion of the valve element, wherein this increased effective pressure area of the valve increases the force rapidly to cause the valve to snap open.

4. A method according to claim 1 in which the the step of rapidly allowing a burst of fluid to flow from the accumulator through the line is at a pressure of between 5 and 300 pounds per square inch.

5. A method according to claim 1 in which the step of rapidly allowing a burst of fluid to flow from the accumulator through the line is at a velocity of between 6 cubic inches per second and 30 cubic inches per second.

6. A method in accordance with claim 1 wherein fluid is pumped into the first reservoir by a first pump and into the second reservoir by a second pump.

* * * * *